US010161888B2

United States Patent
Ikeda et al.

(10) Patent No.: US 10,161,888 B2
(45) Date of Patent: Dec. 25, 2018

(54) CRYSTALLINE PHASE IDENTIFICATION METHOD, CRYSTALLINE PHASE IDENTIFICATION DEVICE, AND X-RAY DIFFRACTION MEASUREMENT SYSTEM

(71) Applicant: Rigaku Corporation, Akishima-shi, Tokyo (JP)

(72) Inventors: Yukiko Ikeda, Inagi (JP); Keigo Nagao, Higashiurawa (JP); Akihiro Himeda, Akishima (JP)

(73) Assignee: RIGAKU CORPORATION, Akishima-Shi, Tokyo (JP)

( * ) Notice: Subject to any disclaimer, the term of this patent is extended or adjusted under 35 U.S.C. 154(b) by 0 days.

(21) Appl. No.: 15/479,473

(22) Filed: Apr. 5, 2017

(65) Prior Publication Data

US 2017/0343492 A1 Nov. 30, 2017

(30) Foreign Application Priority Data

May 24, 2016 (JP) .................................. 2016-103750

(51) Int. Cl.
*G01N 23/207* (2018.01)

(52) U.S. Cl.
CPC ..... *G01N 23/207* (2013.01); *G01N 2223/0566* (2013.01); *G01N 2223/304* (2013.01); *G01N 2223/401* (2013.01); *G01N 2223/605* (2013.01); *G01N 2223/606* (2013.01); *G01N 2223/62* (2013.01)

(58) Field of Classification Search
CPC ............................. G01N 23/20; G01N 23/207
See application file for complete search history.

(56) References Cited

U.S. PATENT DOCUMENTS

| 8,111,807 B2 * | 2/2012 | Ida | G01N 23/207 378/70 |
| 2005/0103995 A1 * | 5/2005 | Yanagiuchi | G01N 23/225 250/309 |
| 2011/0073757 A1 * | 3/2011 | Tanaka | G01N 23/207 250/307 |
| 2012/0022231 A1 * | 1/2012 | Curmi | B82Y 30/00 530/345 |

(Continued)

FOREIGN PATENT DOCUMENTS

JP 2014-178203 A 9/2014

*Primary Examiner* — Christine A Enad
(74) *Attorney, Agent, or Firm* — Buchanan Ingersoll & Rooney PC

(57) ABSTRACT

A crystalline phase contained in a sample is identified, from X-ray diffraction data of the sample which contain data of a plurality of ring-shaped diffraction patterns, using a database in which are registered data related to peak positions and peak intensity ratios of X-ray diffraction patterns for a plurality of crystalline phases. Peak positions and peak intensities for a plurality of the diffraction patterns are detected from the X-ray diffraction data (step 102), and the circumferential angle versus intensity data of the diffraction patterns is created (step 103). The diffraction patterns are grouped into a plurality of clusters on the basis of the circumferential angle versus intensity data (step 105). Crystalline phase candidates contained in the sample are searched from the database on the basis of sets of ratios of peak positions and peak intensities of the diffraction patterns grouped into the same cluster (step 106).

12 Claims, 27 Drawing Sheets

(56) References Cited

U.S. PATENT DOCUMENTS

| | | | | |
|---|---|---|---|---|
| 2013/0028495 A1* | 1/2013 | Star-Lack | ............ | G06T 11/005 382/131 |
| 2014/0278147 A1* | 9/2014 | Sasaki | ................. | G01N 23/207 702/28 |
| 2015/0078526 A1* | 3/2015 | Park | ..................... | G01N 23/207 378/71 |

* cited by examiner

FIG. 4

<RING CHARACTERISTIC FACTORS>

- INTENSITY RANGE R $$R = X_{max} - X_{min}$$

WHERE $X_{max}$ IS THE MAXIMUM VALUE AND $X_{min}$ IS MINIMUM VALUE

- STANDARD VARIANCE $S^2$ $$S^2 = \frac{\sum_{i=1}^{n}(X_i - \bar{X})^2}{n}$$

WHERE n IS THE NUMBER OF DATA POINTS AND $\bar{X}$ IS THE AVERAGE VALUE

- STANDARD DEVIATION S $$S = \sqrt{\frac{\sum_{i=1}^{n}(X_i - \bar{X})^2}{n}}$$

- COEFFICIENT OF VARIATION CV $$CV(\%) = \frac{S}{\bar{X}} \times 100$$

- NUMBER OF PEAKS AND PEAK WIDTH

- SKEWNESS Sk $$Sk = \frac{n}{(n-1)(n-2)} \cdot \sum_{i=1}^{n}\left(\frac{X_i - \bar{X}}{S}\right)^3$$

- KURTOSIS Ku $$Ku = \left\{\frac{n(n+1)}{(n-1)(n-2)(n-3)} \cdot \sum_{i=1}^{n}\left(\frac{X_i - \bar{X}}{S}\right)^4\right\} - \frac{3(n-1)^2}{(n-2)(n-3)}$$

- NORMALIZED AVERAGE $X_{norm}$ $$X_{norm} = \frac{\bar{X}}{X_{max}}$$

- HISTOGRAM

FIG. 7

|  | INTENSITY RANGE R | STANDARD VARIANCE $S^2$ | STANDARD DEVIATION S | COEFFICIENT OF VARIATION CV(%) |
|---|---|---|---|---|
| DIFFRACTION PATTERN OF SINTERED SILICON | 191 | 363 | 19 | 83 |
| DIFFRACTION PATTERN OF POWDER SILICON | 24 | 16 | 4 | 16 |

FIG. 11

| | COEFFICIENT OF VARIATION CV(%) | NOMBER OF PEAKS | PEAK WIDTH (°) |
|---|---|---|---|
| DIFFRACTION PATTERN 1a | 81.9 | 19 | <1 |
| DIFFRACTION PATTERN 2a | 13.5 | 3 | 1.0-3.5 |
| DIFFRACTION PATTERN 3a | 15.9 | 1 | 8.8 |
| DIFFRACTION PATTERN 4a | 16.7 | 1 | 0.4 |

CLASSIFICATION

CLASSIFICATION

FIG. 14

| | COEFFICIENT OF VARIATION CV(%) | SKEW-NESS Sk | KUR-TOSIS Ku | NOR-MALIZED AVERAGE $X_{norm}$ | HISTOGRAM CHARACTERISTICS |
|---|---|---|---|---|---|
| DIFFRAC-TION PATTERN 1a | 81.8 | 3 | 8 | 0.16 | DISTRIBUTION HAS LEFTWARD BIAS, SLIGHTLY WIDE LEADING EDGE, AND LONG RIGHT TAIL |
| DIFFRAC-TION PATTERN 2a | 13.5 | 6 | 43 | 0.16 | DISTRIBUTION HAS LEFTWARD BIAS, NARROW LEADING EDGE, AND LONG RIGHT TAIL |
| DIFFRAC-TION PATTERN 3a | 15.9 | 1 | 0 | 0.75 | DISTRIBUTION HAS RIGHTWARD BIAS AND IS WIDE WITH MOSTLY NO TAILING |
| DIFFRAC-TION PATTERN 4a | 16.7 | 7 | 50 | 0.01 | DISTRIBUTION HAS LEFTWARD BIAS AND IS NARROW |

CLASSIFICATION

CLASSIFICATION

FIG. 18

| | NUMBER OF PEAKS | SKEW-NESS Sk | KUR-TOSIS Ku | NOR-MALIZED AVERAGE $X_{norm}$ | HISTOGRAM CHARACTERISTICS |
|---|---|---|---|---|---|
| DIFFRAC-TION PATTERN 5a | 0 | 4 | 13 | 0.91 | DISTRIBUTION HAS RIGHTWARD BIAS AND IS SLIGHTLY WIDE |
| DIFFRAC-TION PATTERN 6a | 0 | 4 | 20 | 0.23 | DISTRIBUTION HAS LEFTWARD BIAS AND IS SLIGHTLY WIDE |

FIG. 21

| NUMBER | 2θ | NORMALIZED AVERAGE | STANDARD DEVIATION | CLUSTER |
|---|---|---|---|---|
| 1 | 26.00 | 0.86 | 360 | A |
| 2 | 26.32 | 0.90 | 381 | A |
| 3 | 26.68 | 0.16 | 1372 | B |
| 4 | 27.44 | 0.04 | 197 | C |
| 5 | 28.00 | 0.12 | 28 | E |
| 6 | 30.32 | 0.16 | 29 | E |
| 7 | 31.00 | 0.76 | 222 | A |
| 8 | 33.24 | 0.88 | 136 | A |
| 9 | 35.28 | 0.92 | 165 | A |
| 10 | 36.04 | 0.02 | 122 | C |
| 11 | 36.56 | 0.04 | 370 | B |
| 12 | 37.00 | 0.88 | 44 | A |
| 13 | 37.80 | 0.02 | 86 | D |
| 14 | 38.24 | 0.06 | 30 | E |
| 15 | 39.32 | 0.68 | 69 | A |

A: NORMALIZED AVERAGE IS 0.5 OR GREATER

B: NORMALIZED AVERAGE IS LESS THAN 0.5, STANDARD DEVIATION IS 300 OR MORE

C: NORMALIZED AVERAGE IS LESS THAN 0.5, STANDARD DEVIATION IS 100 TO 300

D: NORMALIZED AVERAGE IS LESS THAN 0.5, STANDARD DEVIATION IS 50 TO 100

E: NORMALIZED AVERAGE IS LESS THAN 0.5, STANDARD DEVIATION IS LESS THAN 50

CRYSTALLINE PHASE IDENTIFICATION METHOD, CRYSTALLINE PHASE IDENTIFICATION DEVICE, AND X-RAY DIFFRACTION MEASUREMENT SYSTEM

BACKGROUND OF THE INVENTION

Field of the Invention

The present invention relates to a crystalline phase identification method, a crystalline phase identification device, and an X-ray diffraction measurement system for identifying a crystalline phase contained in a sample composed of a powdery crystal or a polycrystalline substance from X-ray diffraction data of the sample.

Description of the Related Art

Most solid substances exist in a crystalline state. Many solid substances are made of aggregated fine crystal grains. Aggregated fine crystal grains are referred to as a polycrystalline substance. X-ray diffraction measurement for handling powdery crystals or polycrystalline substance as a sample is called X-ray powder diffractometry.

An X-ray diffraction pattern of a sample obtained by measurement using an X-ray diffractometer is characteristic for each crystalline phase. A crystalline phase contained in a sample can be identified by analysis of the X-ray diffraction pattern. As used herein, the term 'crystalline phase' refers to the crystal structure and chemical composition of a substance which is crystalline. JP-A 2014-178203 discloses a technique for carrying out a qualitative analysis for identifying a crystalline phase contained in a sample with good precision on the basis of the powder diffraction pattern of a sample.

When the number of crystal grains in a sample is sufficiently large and the directions of lattice planes are random, a lattice plane having an angle that satisfies diffraction conditions must be present. X-rays diffracted by a lattice plane at a diffraction angle of $2\theta$ proceed along the generating line of a cone in which the half apex angle is $2\theta$ when $2\theta<90°$, and proceed along the generating line of a cone in which the half apex angle is $(180°-2\theta)$ when $2\theta>90°$. In other words, X-rays diffracted by a sample composed of powdery crystal or a polycrystalline substance form numerous cones having different central angles. When such X-rays are received in the detection surface of an X-ray detector, a concentric circular diffraction pattern is obtained. This diffraction pattern is referred to as Debye-Scherrer rings.

Debye-Scherrer rings obtained by X-ray powder diffractometry include a plurality of rings. Uniformity in the circumferential direction of the rings (i.e., the diffraction pattern) reflects the state of particles contained in a sample. When there are lattice planes that yield a diffraction pattern in which intensity is uniform in the circumferential direction and lattice planes that yield a diffraction pattern in which intensity is not uniform in the circumferential direction, the states of grains that contain these lattice planes are different from each other.

Qualitative analysis is an example of an analytic method for identifying a crystalline phase. In a qualitative analysis, the two-dimensional data of an X-ray diffraction pattern of a sample is converted to "diffraction angle $2\theta$ versus intensity I data" to create a "diffraction angle $2\theta$ versus intensity I profile." The position and intensity of peaks in the "profile of the diffraction angle $2\theta$ versus intensity I profile" are detected.

"Diffraction angle $2\theta$ versus intensity I data" may hereinafter be referred to as "$2\theta$-I data." The "diffraction angle $2\theta$ versus intensity I profile" may hereinafter be referred to as the "$2\theta$-I profile."

A system for carrying out a qualitative analysis has a database. "Peak position" data and data for the "ratio of the peak intensity between a plurality of diffraction patterns" in an X-ray diffraction pattern are registered in the database. The "ratio of the peak intensity between a plurality of diffraction patterns" may hereinafter be referred to as "peak intensity ratio."

A system for carrying out a qualitative analysis performs a search in accordance with installed software. Specifically, data related to a plurality of known crystalline phases registered in the database is searched, and candidates of crystalline phases contained in a sample are extracted on the basis of the position of peaks detected from the sample and the peak intensity ratio detected from the sample, like the position of peaks. The search using the database in this case may be referred to as "search and match."

Conventionally, the uniformity of diffraction patterns in the circumferential direction is not taken into consideration when search conditions are set by software during a search and match. Accordingly, it may be possible for unintended crystalline phase candidates to be listed in the search results on the basis of diffraction pattern groups that are not attributable to the same crystalline phase, and, consequently, diffraction pattern groups having different uniformities in the circumferential direction.

SUMMARY OF THE INVENTION

An object of the present invention is to carry out a search of crystalline phase candidates with good precision in identification of crystalline phases and improve analysis precision.

The crystalline phase identification method of the present invention identifies a crystalline phase contained in a sample, from X-ray diffraction data of the sample which contain data of a plurality of ring-shaped diffraction patterns, using a database in which are registered data related to peak positions of X-ray diffraction patterns for a plurality of crystalline phases and data related to peak intensity ratios of X-ray diffraction patterns for a plurality of crystalline phases. Peak positions and peak intensities for a plurality of the diffraction patterns are detected from the X-ray diffraction data. The circumferential angle versus intensity data for a plurality of the diffraction patterns are created from the X-ray diffraction data. The diffraction patterns are grouped into a plurality of clusters (namely, groups) on the basis of the circumferential angle ($\beta$) versus intensity (I) data thus created. Crystalline phase candidates contained in the sample are searched from the database on the basis of sets of ratios of peak positions and peak intensities of the diffraction patterns grouped into the same cluster.

The crystalline phase identification device of the present invention identifies a crystalline phase contained in a sample, from X-ray diffraction data of the sample which contain data of a plurality of ring-shaped diffraction patterns, using a database in which are registered data related to peak positions of X-ray diffraction patterns for a plurality of crystalline phases and data related to peak intensity ratios of X-ray diffraction patterns for a plurality of crystalline phases. The crystalline phase identification device comprises: detection means for detecting peak positions and peak intensities for a plurality of the diffraction patterns from the X-ray diffraction data, and creating circumferential angle versus intensity data of the diffraction patterns; clustering means for grouping the diffraction patterns into a plurality of clusters on the basis of the circumferential angle (β) versus intensity (I) data thus created by the detection means; and searching means for searching for crystalline phase candidates contained in the sample from the database on the basis of sets of ratios of peak positions and peak intensities of the diffraction patterns grouped into the same cluster by the clustering means.

Following are the characteristics of the present invention.

(1) Peak positions and peak intensities are detected for a plurality of diffraction patterns from the X-ray diffraction data, and circumferential angle versus intensity data of the diffraction patterns are created. As used herein, the phrase "plurality of diffraction patterns" refers to the rings contained in concentric circular Debye-Scherrer rings. The X-ray diffraction data is not limited to two-dimensional image data obtained by two-dimensional image measurement, and may be one-dimensional data or the like obtained by scanning the diffraction patterns with a detector.

(2) Diffraction patterns are grouped into a plurality of clusters on the basis of the circumferential angle versus intensity data thus created. The diffraction patterns are thereby grouped into a plurality of clusters in accordance with the uniformity of the diffraction pattern in the circumferential direction.

(3) Crystalline phase candidates contained in the sample are searched from a database on the basis of the sets of ratios of peak positions and peak intensities of the diffraction patterns grouped into the same cluster. A search of crystalline phase candidates is thereby carried out on the basis of the sets of diffraction patterns that are closely uniform in the circumferential direction. Therefore, a search for crystalline phase candidates is carried out with good precision in the identification of a crystalline phase, and analysis precision can be enhanced.

Furthermore, in another aspect of the crystalline phase identification method and crystalline phase identification device of the present invention, ring characteristic factors representing homogeneity of intensity in the circumferential direction of the diffraction patterns are determined from the circumferential angle versus intensity data of the diffraction patterns, and the diffraction patterns are grouped into a plurality of clusters in accordance with the ring characteristic factors thus determined.

The term "ring characteristic factor" is a neologism in the present specification. The term "ring characteristic factor" refers to an element that expresses the homogeneity of intensity of diffraction patterns in the circumferential direction. The uniformity of diffraction patterns in the circumferential direction is made clear by ring characteristic factors. Therefore, the diffraction patterns are grouped into a plurality of clusters in accordance with the determined ring characteristic factors, whereby diffraction patterns having different uniformity in the circumferential direction can be grouped into a plurality of clusters.

Furthermore, in yet another aspect of the crystalline phase identification method and crystalline phase identification device of the present invention, an intensity range, a standard variance, a standard deviation, or a coefficient of variation, where intensity is a variate, are calculated as the ring characteristic factors from the circumferential angle versus intensity data of the diffraction patterns.

Calculating the intensity range, standard variance, standard deviation, or coefficient of variation as ring characteristic factors allows the degree of uniformity of diffraction patterns in the circumferential direction to be quantified.

Furthermore, in yet another aspect of the crystalline phase identification method and crystalline phase identification device of the present invention, a number of peaks and a peak width in a circumferential angle versus intensity profile are calculated as the ring characteristic factors from the circumferential angle versus intensity data of the diffraction patterns.

Using the number of peaks and the peak width in a circumferential angle versus intensity profile as the ring characteristic factors allows diffraction patterns in which the intensity range, standard variance, standard deviation, or coefficient of variation are about the same value to be grouped into different clusters from differences in the number of peaks and the peak width.

Furthermore, in yet another aspect of the crystalline phase identification method and crystalline phase identification device of the present invention, an intensity histogram is created as the ring characteristic factor from the circumferential angle versus intensity data of the diffraction patterns.

Using an intensity histogram as the ring characteristic factor allows diffraction patterns in which the intensity range, standard variance, standard deviation, or coefficient of variation are about the same value to be grouped into different clusters from differences in the histogram. Diffraction patterns in which the number of peaks in the circumferential angle versus intensity profile is calculated to be "0" can also be grouped by differences in the histogram.

Furthermore, in yet another aspect of the crystalline phase identification method and crystalline phase identification device of the present invention, a skewness, kurtosis, or normalized average $X_{norm}$ of the intensity distribution are calculated as the ring characteristic factors from the circumferential angle versus intensity data of the diffraction patterns. Using a skewness, kurtosis, or normalized average $X_{norm}$ of the intensity distribution as the ring characteristic factors allows characteristics of the intensity distribution to be quantified and used in clustering.

Next, the X-ray diffraction measurement system of the present invention comprises an X-ray diffractometer for measuring the X-ray diffraction data of a sample, and the crystalline phase identification device of any of the above-described aspects.

Effects of the Invention

In accordance with the present invention, a search for crystalline phase candidates can be carried out with good precision in the identification of a crystalline phase, and analysis precision can be enhanced.

BRIEF DESCRIPTION OF THE DRAWINGS

FIG. 4 is a diagram showing ring characteristic factors used in an embodiment of the crystalline phase identification method of the present invention;

FIG. 7 is a diagram showing an example of the intensity range, standard variance, standard deviation, and coefficient of variation in the diffraction pattern of sintered silicon and the diffraction pattern of powder silicon;

FIG. 11 is a diagram showing the following factors for the diffraction patterns 1a to 4a of FIG. 8, namely, the coefficient of variation, the number of peaks in the β-I profile, and the peak width in the β-I profile;

FIG. 14 is a diagram showing the characteristics of each of the following elements for the diffraction patterns 1a to 4a of FIG. 8, namely, the coefficient of variation, the skewness of the intensity distribution, the kurtosis of the intensity distribution, the normalized average of the intensity distribution, and the histogram;

FIG. 18 is a diagram showing the characteristics of each of the following elements for the diffraction pattern 5a of FIG. 15A and the diffraction pattern 6a of FIG. 15B, namely, the number of peaks, the skewness of the intensity distribution, the kurtosis of the intensity distribution, the normalized average of the intensity distribution, and the histogram;

FIG. 21 is a diagram showing an example of grouping using the normalized average and standard deviation as ring characteristic factors;

DESCRIPTION OF THE PREFERRED EMBODIMENTS (First Embodiment)
(Configuration of the X-Ray Diffraction Measurement System)

Figure 1A:
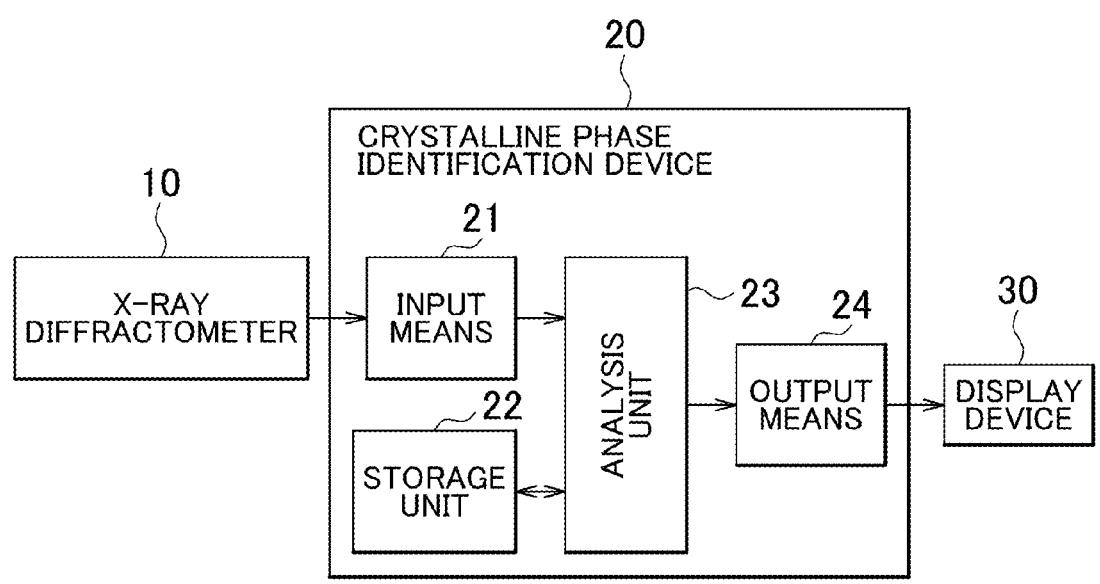
FIG. 1A is a block diagram showing a configuration of an embodiment of an X-ray diffraction measurement system of the present invention.

FIG. 1A is a block diagram showing a schematic configuration of an embodiment of an X-ray diffraction measurement system of the present invention. The X-ray diffraction measurement system comprises an X-ray diffractometer 10, a crystalline phase identification device 20, and a display device 30. The display device 30 is composed of, e.g., a flat panel display device or the like. The display device 30 may be integrally configured with the crystalline phase identification device 20.

Figure 1B:
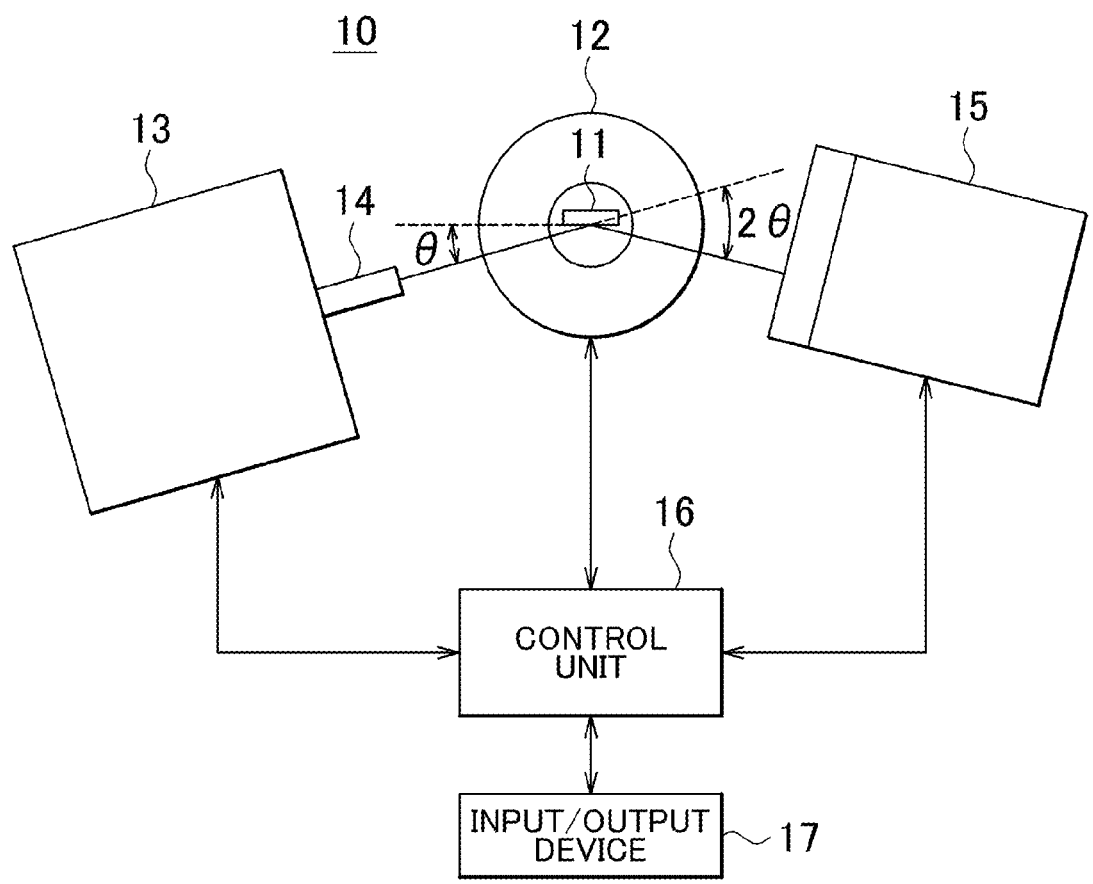
FIG. 1B is a diagram showing an example of the configuration of the X-ray diffractometer of FIG. 1A.

FIG. 1B is a diagram showing a schematic configuration of the X-ray diffractometer. The X-ray diffractometer 10 is configured to include a goniometer 12, an X-ray generator 13, a collimator 14, an X-ray detector 15, a control unit 16, and an input/output device 17. The goniometer 12 is an angle-measuring instrument. A sample stage for mounting and rotating a sample 11 is disposed in the center part of the goniometer 12. X-rays generated from the X-ray generator 13 are passed through the collimator 14 having a pinhole to form a narrow beam-like flux and are irradiated on the sample 11.

The X-ray detector 15 detects X-rays diffracted by the sample 11. When X-rays are irradiated on the sample 11 at angle of "θ" relative to a lattice plane in the sample 11, the diffraction angle of X-rays are "2θ". The control unit 16 is composed of a computer, a sequencer, a dedicated circuit, or the like, and controls the goniometer 12, the X-ray generator 13, and the X-ray detector 15. The input/output device 17 inputs measurement conditions or the like to the control unit 16, and outputs X-ray diffraction data detected by the X-ray detector 15 to the crystalline phase identification device 20.

FIG. 1B shows a reflective-type X-ray diffractometer, but in lieu thereof, the device may be a transmission-type X-ray diffractometer. The X-ray detector is not limited to being a two-dimensional detector, and it is also possible to use a zero-dimensional detector or a one-dimensional detector. In such a case, it is necessary to move, e.g., rotate the sample or detector in relation to the center line of the sample.

Figure 2A:
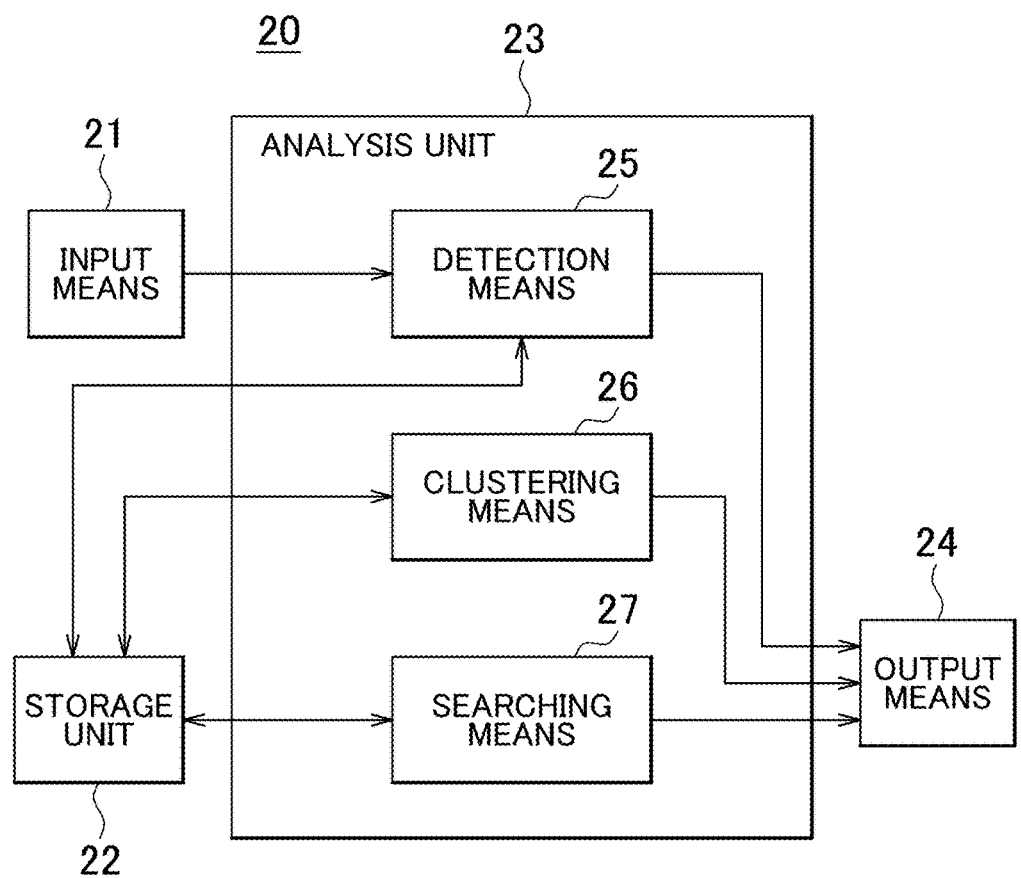
FIG. 2A is a block diagram showing a configuration of an embodiment of a crystalline phase identification device of the present invention.

FIG. 2A is a block diagram showing a schematic configuration of an embodiment of a crystalline phase identification device 20 of the present invention. The crystalline phase identification device 20 is configured to include input means 21, a storage unit 22, an analysis unit 23, and output means 24. The crystalline phase identification device 20 can be realized by a typical computer. In such a case, the input means 21 and the output means 24 may be constituted by, e.g., an input/output interface or the like. The storage unit 22 may be constituted by, e.g., a hard disk, a memory, or the like. The analysis unit 23 may be constituted by, e.g., a CPU or the like.

A database is stored in the storage unit 22. Data related to known X-ray diffraction patterns of a plurality of crystalline phases is registered in the database. Specifically, the data of peak positions and peak intensity ratios in a 2θ-I profile derived from the X-ray diffraction patterns of a plurality of crystalline phases are registered. More specifically, the data of the peak positions and peak intensity ratios are registered as data of the distance "d" versus intensity ratio "I" of the lattice plane (i.e., d-I data). The storage unit 22 may be an external hard disk or the like.

Analysis unit 23 is configured to include detection means 25, clustering means 26, and searching means 27. The analysis unit 23 stores X-ray diffraction data inputted from the X-ray diffractometer 10 via the input means 21 in the storage unit 22. The analysis unit 23 subjects the X-ray diffraction data stored in the storage unit 22 to a later-described process and stores the processing results in the storage unit 22. The analysis unit 23 also displays the processing results on the display device 30 via the output means 24.

(Operation of the Analysis Unit 23)

Figure 3:
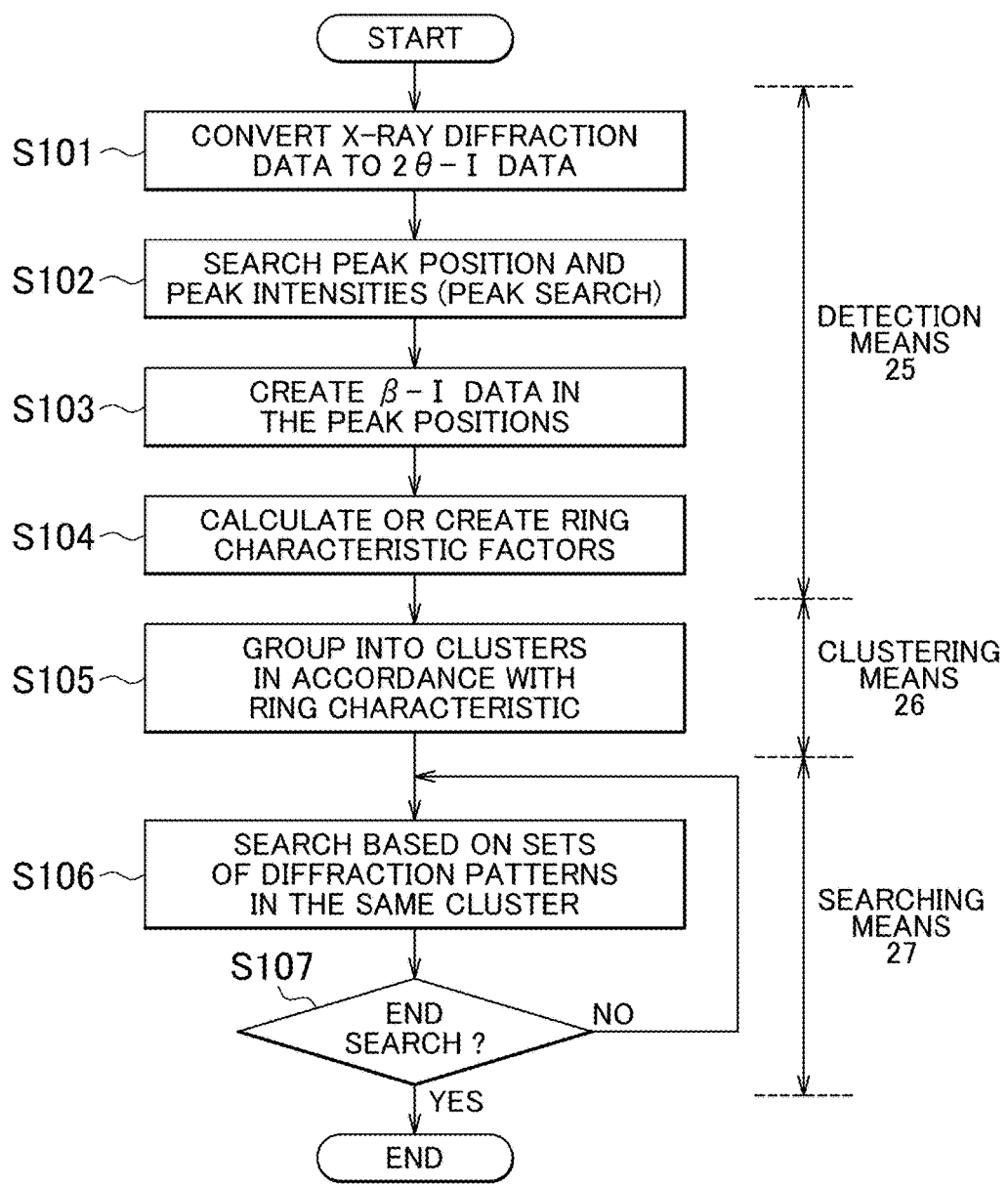
FIG. 3 is a flowchart showing the operation of an example of the analysis unit 23 of FIG. 1.

FIG. 3 is a flowchart showing the operation of the analysis unit 23 in the first embodiment of the present invention. First, the detection means 25 of the analysis unit 23 reads the X-ray diffraction data stored in the storage unit 22, preprocesses the X-ray diffraction data, and thereafter converts the X-ray diffraction data to 2θ-I data (step 101). As used herein, the term 'preprocessing' refers to background correction or the like; the background correction being a process for removing, e.g., noise.

In general, background correction includes uniform background correction, median filter correction, and the like. In the specific examples described below, uniform background correction is carried out unless otherwise particularly noted. When the X-ray diffractometer 10 is provided with a data processing unit and preprocessing has already been carried out by the X-ray diffractometer 10, preprocessing is not required to be carried out again.

Next, the detection means 25 detects the peak positions and peak intensities in the 2θ-I profile (i.e., the 2θ-I data) (step 102). This process is conventionally referred to as a 'peak search.' The detection means 25 subsequently creates circumferential angle β versus intensity I data (hereinafter referred to as "β-I data") of the diffraction patterns in the peak positions of the 2θ-I profile detected in step 102 (step 103).

Figure 2B:
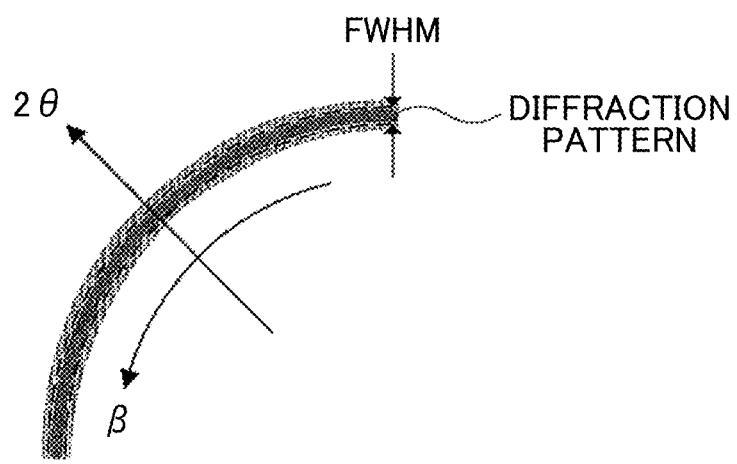
FIG. 2B is a diagram showing the direction of the diffraction angle 2θ and the direction of the angle β.

FIG. 2B is a diagram showing the direction of the diffraction angle 2θ and the direction of the angle β. In this case, the intensity "I" of the β-I data is the integrated intensity in the range of the full-width at half maximum (FWHM) of the peak width at the peak positions of, e.g., the 2θ-I profile. The integration range may be narrowed to make the range FWHM/2, or the integration range may be increased to make the range 2FWHM.

The range of the angle β obtained by measurement using the X-ray diffractometer 10 differs in accordance with the area of the X-ray detector 15 of the X-ray diffractometer 10, the distance (camera length) between the sample 11 and the X-ray detector 15, and whether the measurement method is a transmission method or a reflection method. However, the range of the angle β is preferably used in order to analyze the widest possible range in the resulting measurement data.

In FIG. 3, the detection means 25 subsequently calculates or creates ring characteristic factors (described hereunder) from the β-I data (step 104). Next, the clustering means 26 of the analysis unit 23 groups the diffraction patterns into a plurality of clusters in accordance with the ring characteristic factors calculated or created in step 104 (step 105). When, e.g., three ring characteristic factors are used in the clustering process, three-dimensional vectors with the ring characteristic factors as variables are created, and the diffraction patterns proximate in distance between the distal ends of vectors are grouped into the same cluster.

Next, the searching means 27 of the analysis unit 23 searches for crystalline phases in the database that show peak positions and peak intensity ratios with a high coincidence with the sets of peak positions and peak intensity ratios (detected in step 102) of the diffraction patterns grouped into the same clusters, with the assumption that all or a portion of the diffraction patterns contained in the same clusters are derived from the same crystalline phase (step 106). As a result of this search, crystalline phase candidates are extracted. Lastly, the searching means 27 assesses whether to end the search (step 107), and when further crystalline phase candidates are to be searched, the process returns to step 106.

(Ring Characteristic Factors)

FIG. 4 is a diagram showing the ring characteristic factors used in an embodiment of the present invention. In the present embodiment, the values shown in FIG. 4 are used as the ring characteristic factors, where the intensity I in the β-I data is a variate "x", the values namely being the intensity range (R), standard variance ($s^2$), standard deviation (s), coefficient of variation (CV), number of peaks in a circumferential angle (β) versus intensity (I) profile (hereinafter referred to as "β-I profile"), peak width in the β-I profile, skewness (distortion) Sk of the intensity distribution, kurtosis (sharpness) Ku of the intensity distribution, normalized average $X_{norm}$ of the intensity distribution, and histogram of the intensity.

(Example 1 of Ring Characteristic Factors)

Figure 5A:
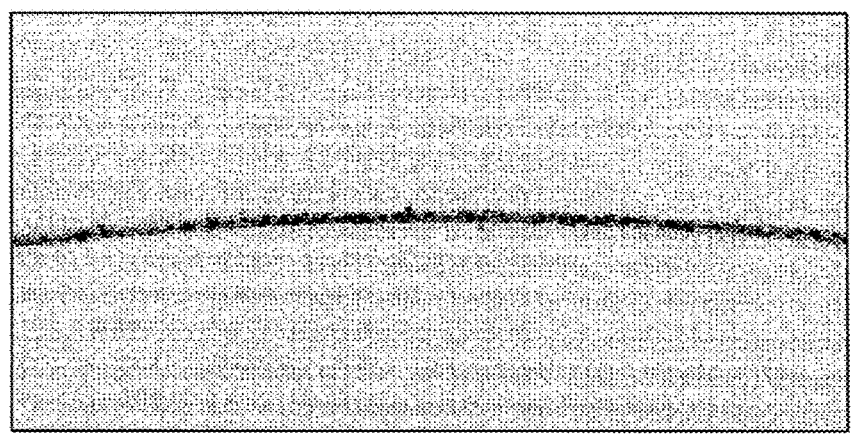
FIG. 5A is a view showing an example of a diffraction pattern of sintered silicon.
Figure 5B:
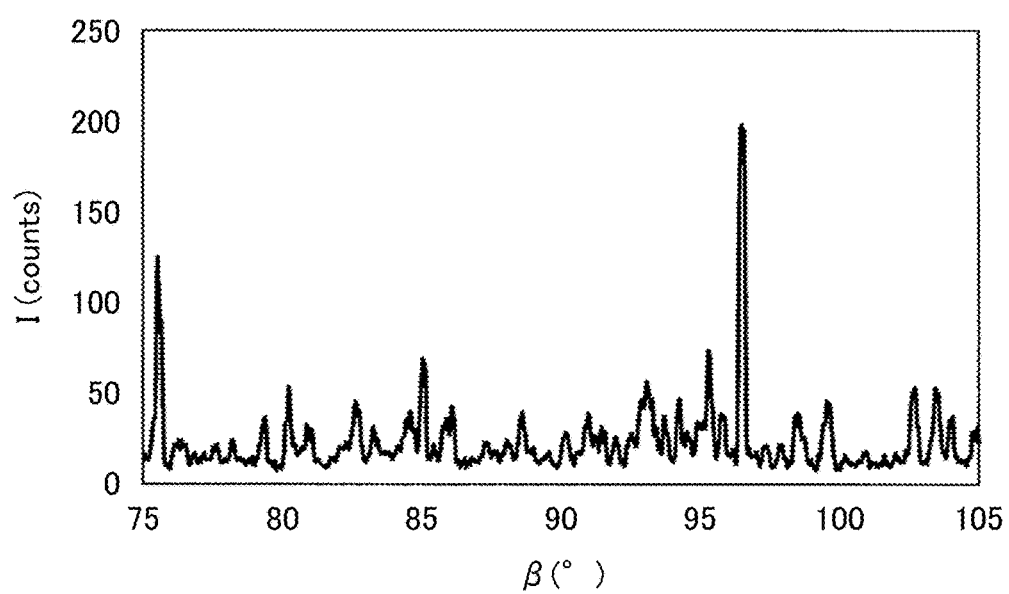
FIG. 5B is a diagram showing an example of a β-I profile of a diffraction pattern of sintered silicon.

Sintered silicon and powder silicon having an average grain diameter of 5 μm were measured as an example of measuring samples with different particle states. As a result of the measurement, two X-ray diffraction patterns having two different uniformities in the circumferential direction were obtained. FIG. 5A is a view showing an example of a diffraction pattern of sintered silicon. FIG. 5B is a diagram showing an example of a β-I profile of a diffraction pattern of sintered silicon.

Figure 6A:
FIG. 6A is a view showing an example of a diffraction pattern of powder silicon.
Figure 6B:
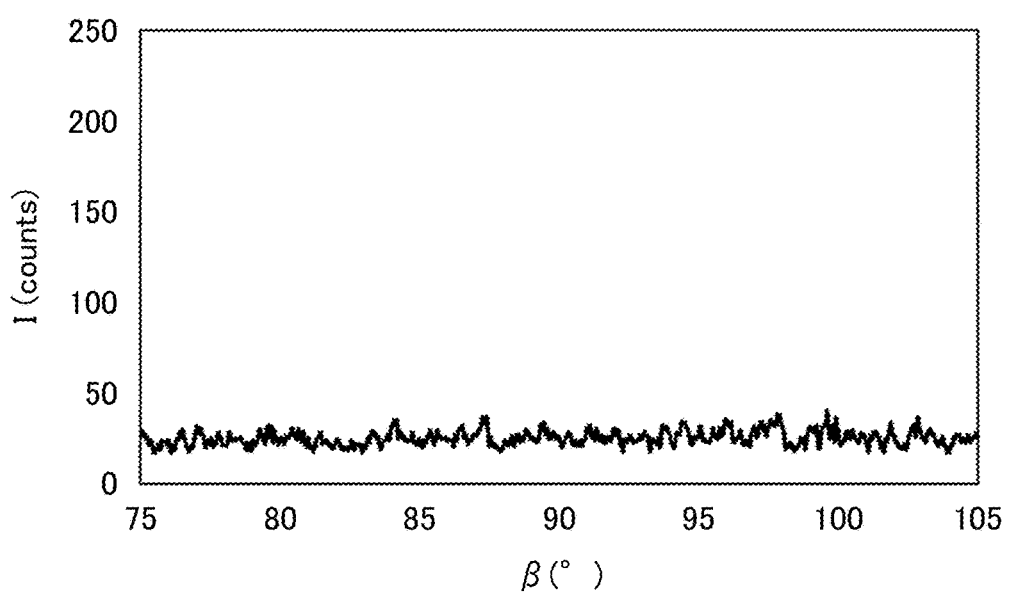
FIG. 6B is a diagram showing an example of a β-I profile of a diffraction pattern of powder silicon.

FIG. 6A is a view showing an example of a diffraction pattern of powder silicon. FIG. 6B is a diagram showing an example of a β-I profile of a diffraction pattern of powder silicon. The diffraction pattern of sintered silicon shown in FIG. 5A had low uniformity in the circumferential direction in comparison with the diffraction pattern of powder silicon shown in FIG. 6A. The above-described intensity range R, standard variance $s^2$, standard deviation s, and coefficient of variation CV were calculated in the range of β=75° to 105° from the β-I data of the diffraction patterns.

FIG. 7 is a diagram showing an example of the intensity range R, standard variance $s^2$, standard deviation s, and coefficient of variation CV in the β-I data of the diffraction pattern of sintered silicon and the diffraction pattern of powder silicon. The intensity range R, standard variance $s^2$, standard deviation s, and coefficient of variation CV of the sintered silicon, which has low uniformity in the circumferential direction, all have high values in comparison with the powder silicon. It is apparent that uniformity in the circumferential direction is lower in commensurate fashion to higher values of the ring characteristic factors. Thus, using the intensity range R, standard variance $s^2$, standard deviation s, and coefficient of variation CV allows the degree of uniformity of the diffraction pattern in the circumferential direction to be quantified. Therefore, the use of these ring characteristic factors makes it possible to group diffraction patterns having different uniformities in the circumferential direction into a plurality of clusters.

(Example 2 of Ring Characteristic Factors)

Figure 8:
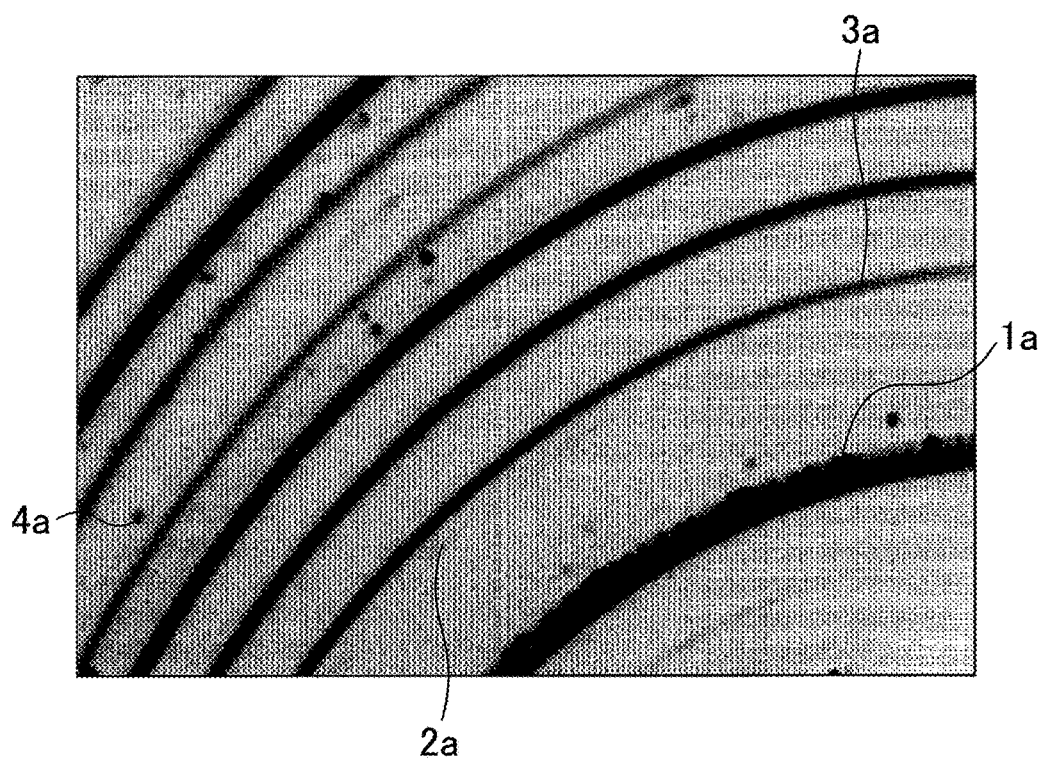
FIG. 8 is a view showing an example of the diffraction pattern of a mixed powder sample of a mineral.

A mixed powder sample of a mineral was measured while being rotated in an in-plane direction, and X-ray diffraction patterns having a plurality of Debye-Scherrer rings differing in uniformity in the circumferential direction were obtained. FIG. 8 is a view showing an example of the diffraction patterns of a mixed powder sample of a mineral. The diffraction pattern 1a was a ring shape in which intensity varies irregularly in the circumferential direction. The diffraction pattern 2a was a ring shape in which intensity varies intermittently in the circumferential direction. The diffraction pattern 3a was a ring shape in which the intensity is uniform in the circumferential direction. The diffraction pattern 4a was an independent spot shape.

Figure 9A:
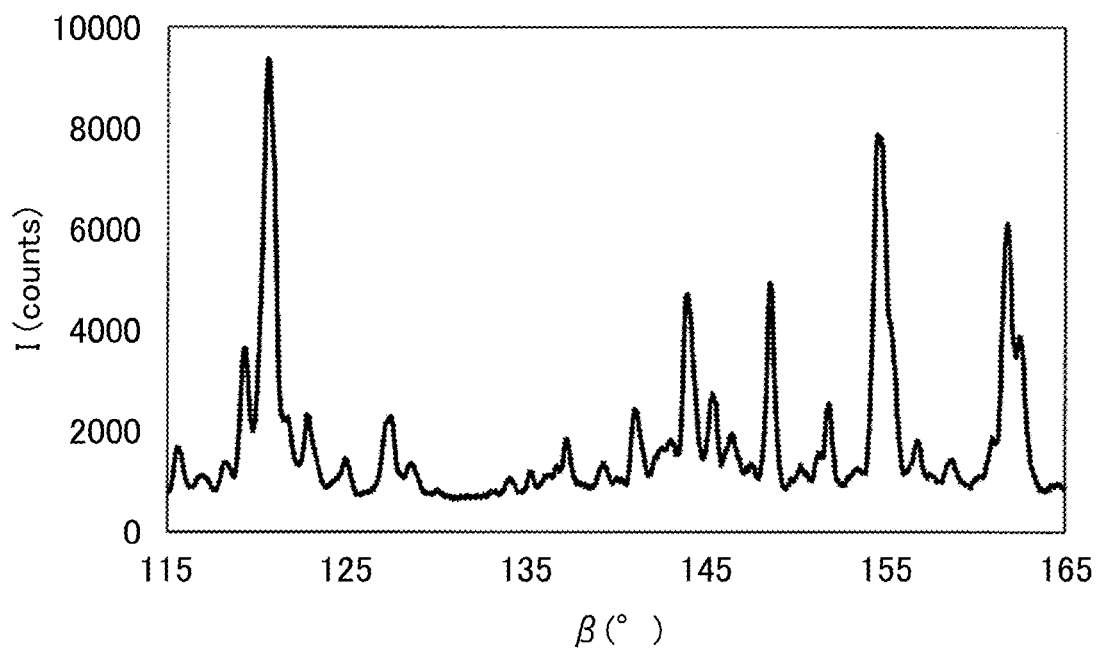
FIG. 9A is a diagram showing the β-I profile of diffraction pattern 1a of FIG. 8.
Figure 9B:
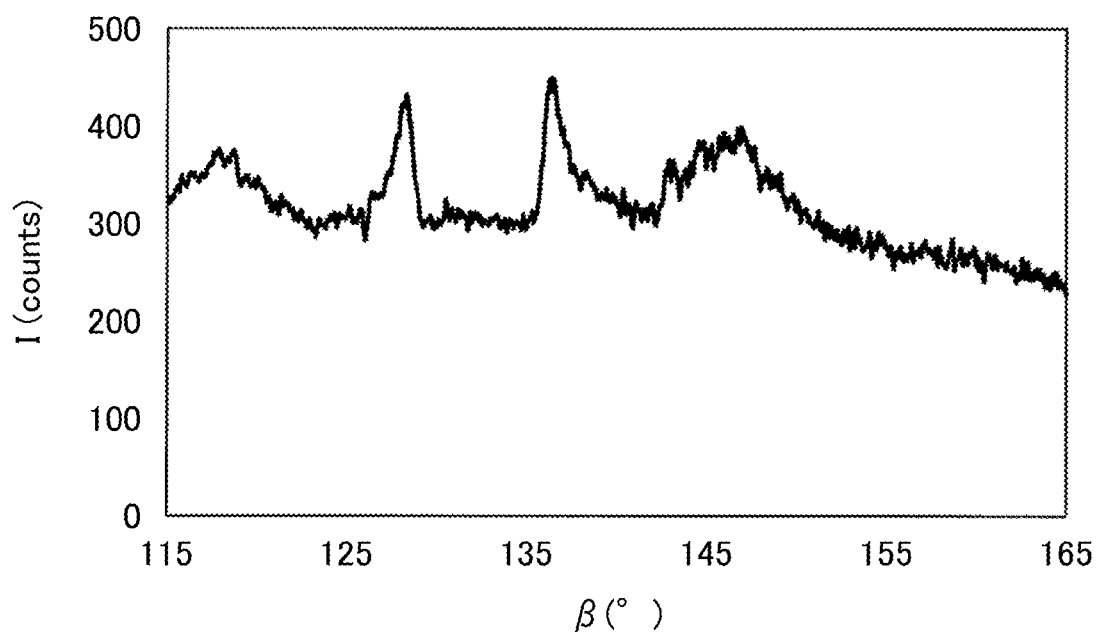
FIG. 9B is a diagram showing the β-I profile of diffraction pattern 2a of FIG. 8.
Figure 10A:
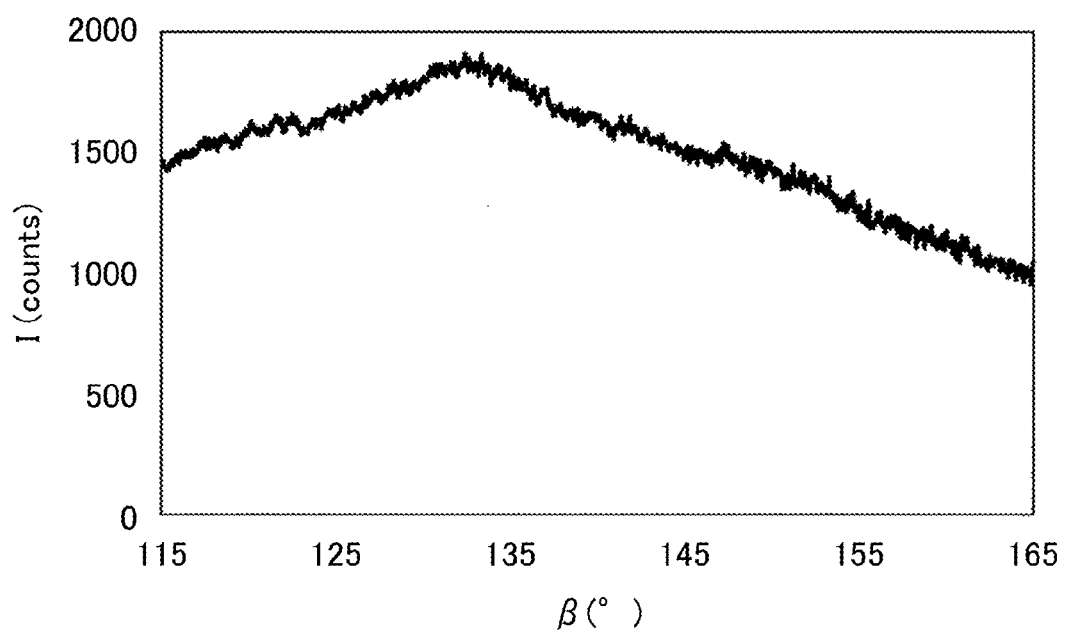
FIG. 10A is a diagram showing the β-I profile of diffraction pattern 3a of FIG. 8.
Figure 10B:
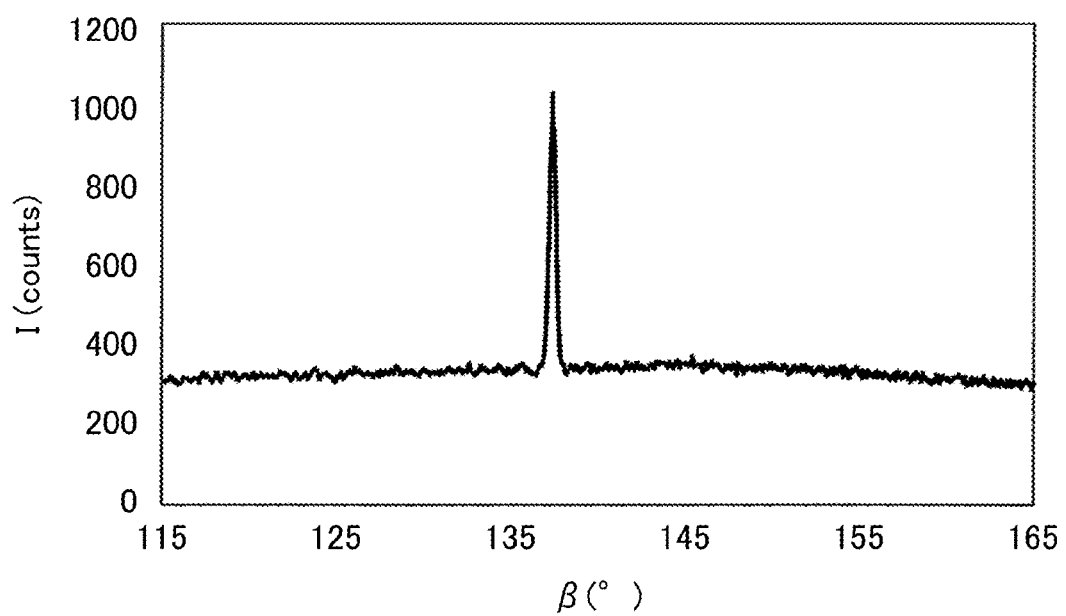
FIG. 10B is a diagram showing the β-I profile of diffraction pattern 4a of FIG. 8.

FIG. 9A is a diagram showing the β-I profile of the diffraction pattern 1a. FIG. 9B is a diagram showing the β-I profile of the diffraction pattern 2a. FIG. 10A is a diagram showing the β-I profile of diffraction pattern 3a. FIG. 10B is a diagram showing the β-I profile of diffraction pattern 4a. The coefficient of variation CV in the β-I data, the number of peaks in the β-I profile, and the peak width in the β-I profile were calculated in the range of β=115° to 165° from the β-I data of the diffraction patterns. The peak-top method for detecting only peaks at 3σ (sigma) or greater in relation to the magnitude "σ" of the noise level was used for calculating the number of peaks and the width of peaks.

FIG. 11 is a diagram showing the following values for the diffraction patterns 1a to 4a; namely, values of the coefficient of variation CV, values of the number of peaks in the β-I profile, and values of the peak width in the β-I profile. FIG. 11 is a diagram showing the values of the following diffraction patterns 1a to 4a, namely, the values of the coefficient of variation CV, the number of peaks in the β-I profile, and the peak width in the β-I profile. The coefficient of variation CV had a high value of 81.9 in the ring-shaped diffraction pattern 1a in which the intensity varied irregularly in the circumferential direction. In contrast, the value was 13.5 in the diffraction pattern 2a, 15.9 in the diffraction pattern 3a, and 16.7 in the diffraction pattern 4a. These values were less than that in diffraction pattern 1a. There was not a large difference between diffraction patterns 2a, 3a and 4a.

On the other hand, in relation to the number of peaks and the peak width in the ring-shaped diffraction pattern 1a in which the intensity varies irregularly in the circumferential direction, the number of peaks was high at 19 and the peak width was narrow at less than 1°. In the ring-shaped diffraction pattern 2a in which the intensity varies intermittently in the circumferential direction, the number of peaks was 3 and the peak width was not uniform being 1.0° to 3.5°. In the ring-shaped diffraction pattern 3a in which the intensity is uniform in the circumferential direction, the number of peaks was 1 and the peak width was relatively broad at 8.8. In the spot-shaped diffraction pattern 4a, the number of peaks is 1 and the peak width was narrow at 0.4. It is apparent from this specific example that the diffraction patterns 2a, 3a, 4a in which the coefficient of variations CV are about the same value can be grouped into different clusters based the differences in the number of peaks and the peak widths in the β-I profile.

(Example 3 of Ring Characteristic Factors)

Variability in the circumferential direction of Debye-Scherrer rings can be analyzed by creating an intensity histogram of the β-I data. In the diffraction patterns 1a to 4a of FIG. 8, median filter correction was carried out and the ranges of intensity from 0 (zero) to the maximum value in the β-I data of the diffraction patterns were divided into 50 to create a histogram.

Figure 12A:
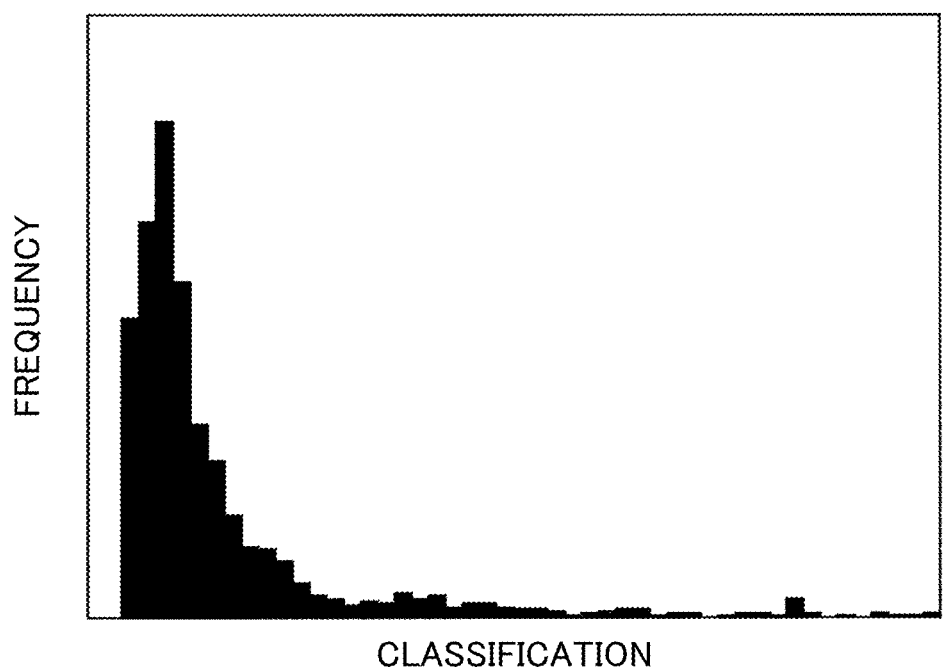
FIG. 12A is a diagram showing a histogram created from the β-I data of the diffraction pattern 1a of FIG. 8.
Figure 12B:
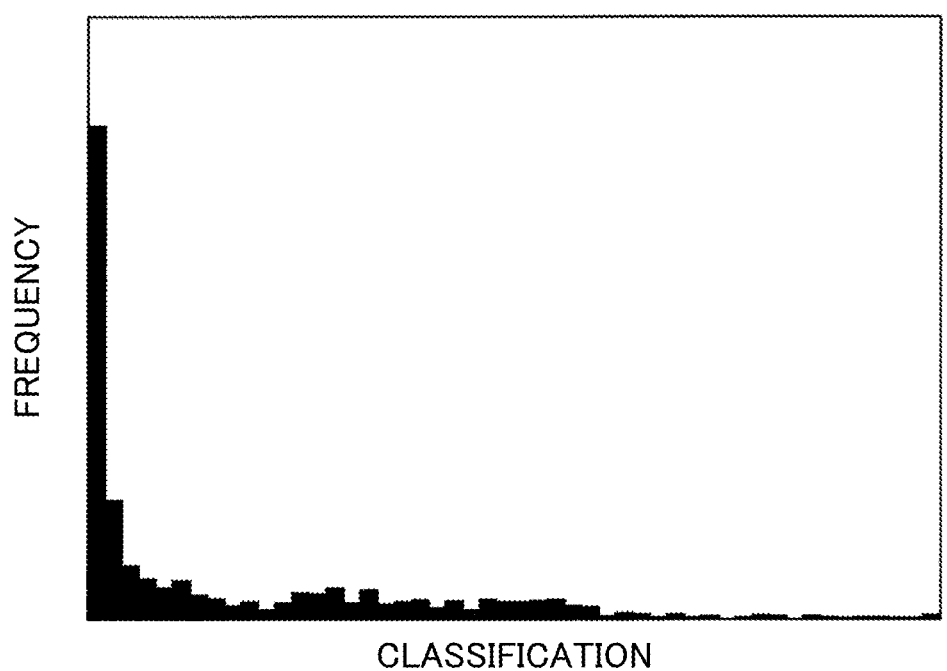
FIG. 12B is a diagram showing a histogram created from the β-I data of the diffraction pattern 2a of FIG. 8.
Figure 13A:
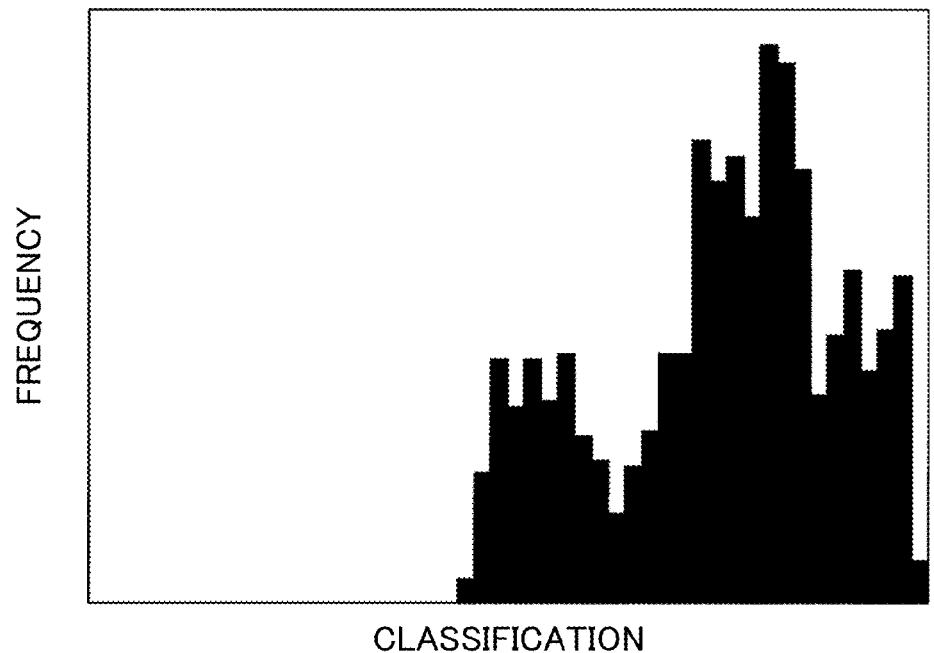
FIG. 13A is a diagram showing a histogram created from the β-I data of the diffraction pattern 3a of FIG. 8.
Figure 13B:
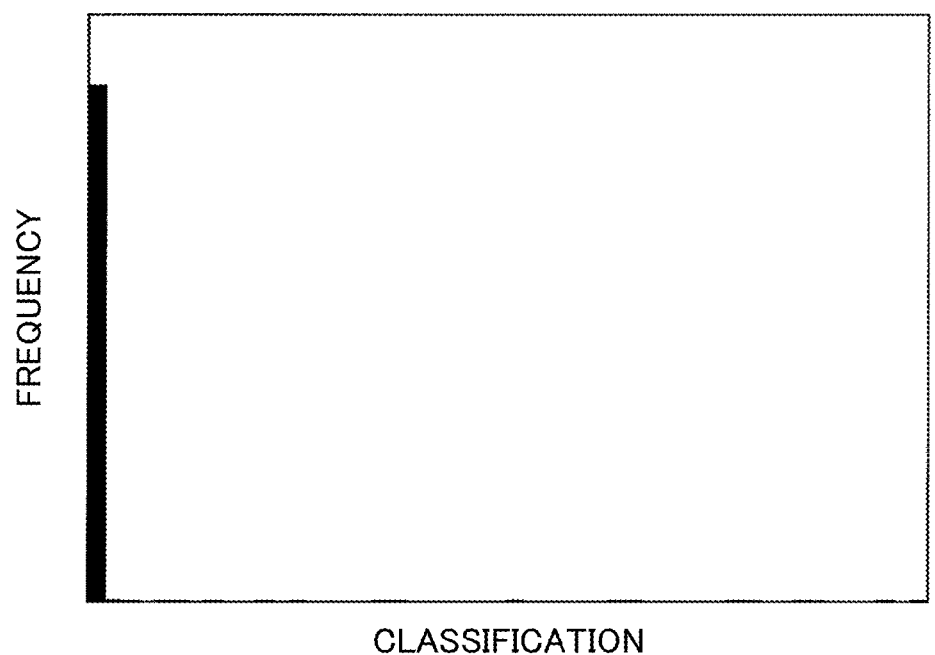
FIG. 13B is a diagram showing a histogram created from the β-I data of the diffraction pattern 4a of FIG. 8.

FIG. 12A is a diagram showing a histogram created from the β-I of the diffraction pattern 1a. FIG. 12B is a diagram showing a histogram created from the β-I data of the diffraction pattern 2a. FIG. 13A is a diagram showing a histogram created from the β-I data of the diffraction pattern 3a. FIG. 13B is a diagram showing a histogram created from the β-I data of the diffraction pattern 4a.

(Skewness Sk, Kurtosis Ku, and Normalized Average $X_{norm}$)

The skewness Sk indicates the amount of leftward or rightward bias in the intensity distribution of the β-I data of a diffraction pattern. When Sk>0, the β-I data has a distribution with a long right tail. When Sk<0, the β-I data has a distribution with a long left tail.

Kurtosis Ku indicates the peakedness (sharpness) of the intensity distribution in the β-I data of a diffraction pattern. When Ku>0, the intensity distribution of the β-I data is more peaked than a normal distribution, and when Ku<0, the intensity distribution of the β-I data is flatter than a normal distribution.

The normalized average $X_{norm}$ is a value obtained by dividing the average value by the maximum value of the intensity. The closer the normalized average $X_{norm}$ is to "0 (zero)," the more leftward the intensity distribution of the β-I data is, and the closer to "1" the more rightward the intensity distribution of the β-I data is.

Using the skewness Sk of the intensity distribution, kurtosis Ku of the intensity distribution, or the normalized average $X_{norm}$ of the intensity distribution as ring characteristic factors allows the characteristics of the intensity distribution to be quantified and used in clustering. As used herein, the term "intensity distribution" refers to the features or tendencies of intensity as expressed in a frequency distribution table, a graph, or the like.

FIG. 14 is a diagram showing the characteristics of the following values for the diffraction patterns 1a to 4a; namely, the characteristics of the values of the coefficient of variation CV, the characteristics of the skewness Sk of the intensity distribution, the characteristics of the kurtosis Ku of the intensity distribution, the characteristics of the normalized average $X_{norm}$ of the intensity distribution, and the characteristics of the histogram. The following can be said for the ring-shaped diffraction pattern 1a in which the intensity varies irregularly in the circumferential direction. Namely, the skewness Sk is a positive value of 3, which therefore suggests a distribution with a long right tail. The kurtosis Ku is a somewhat low positive value of 8, which therefore suggests a slightly more peaked distribution than a normal distribution. Also, the normalized average $X_{norm}$ is a low value of 0.16, which therefore suggests a distribution in which the average is biased leftward. In actuality, the shape of the histogram also indicates a distribution that is leftward, has a slightly wide leading edge, and has a long right tail.

The following can be said for the ring-shaped diffraction pattern 2a in which the intensity varies intermittently in the circumferential direction. Namely, the skewness Sk is a positive value 6, which therefore suggests a distribution with a long right tail. The kurtosis Ku is a high positive value 43, which therefore suggests a more peaked distribution than a normal distribution. Also, the normalized average $X_{norm}$ is a low value of 0.16, which therefore suggests a distribution in which the average is biased leftward. In actuality, the shape of the histogram also indicates a distribution that is leftward, has a narrow leading edge, and has a long right tail.

The following can be said for the ring-shaped diffraction pattern 3a in which the intensity is uniform in the circumferential direction. Namely, the skewness Sk is a low positive value 1, which therefore suggests a distribution with a long right tail yet nearly symmetrical. The kurtosis Ku is 0, which therefore suggests a distribution that is proximate to a normal distribution. Also, the normalized average $X_{norm}$ is a large value of 0.75, which therefore suggests a distribution in which the average is biased rightward. In actuality, the shape of the histogram also indicates a distribution that is rightward and wide with mostly no tailing.

The following can be said for the spot-shaped diffraction pattern 4a. Namely, the skewness Sk is a slightly low positive value 7, which therefore suggests a distribution with a long right tail. The kurtosis Ku is a high positive value of 50, which therefore suggests a distribution that is more greatly peaked than a normal distribution. Also, the normalized average $X_{norm}$ is a very low value of 0.01, which therefore suggests a distribution in which the average is inordinately biased leftward. In actuality, the shape of the histogram also indicates a distribution that is leftward and narrow.

In view of the specific examples above, it is apparent that the diffraction patterns 2a, 3a, 4a can be grouped into different clusters from the difference in histogram shapes, as well as from the values of the skewness Sk, kurtosis Ku, and normalized average $X_{norm}$ in relation to the diffraction patterns 2a, 3a, 4a in which the coefficients of variation CV are about the same value.

(Example 4 of Ring Characteristic Factors)

Figure 15A:
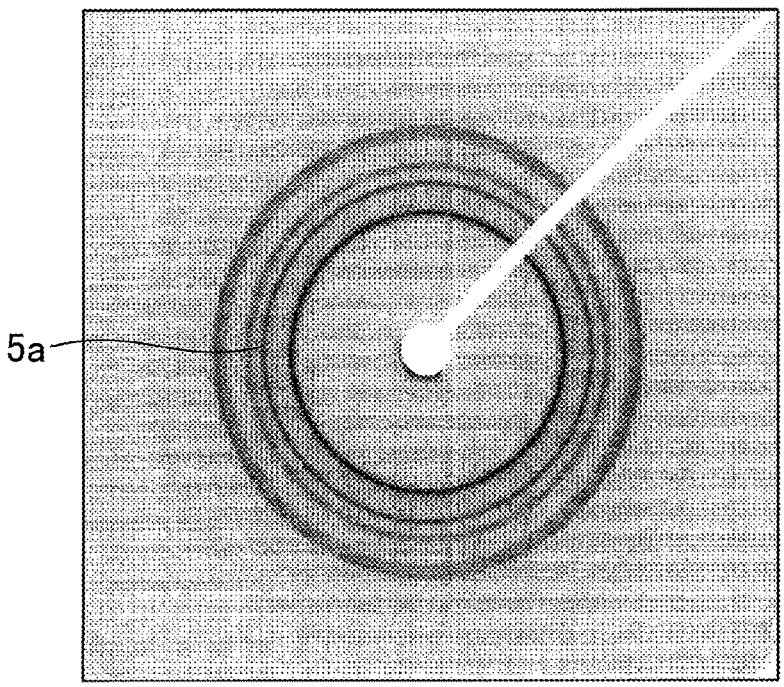
FIG. 15A is a diagram showing an example of the diffraction pattern of a sheet-shaped sample composed of unoriented polypropylene.
Figure 15B:
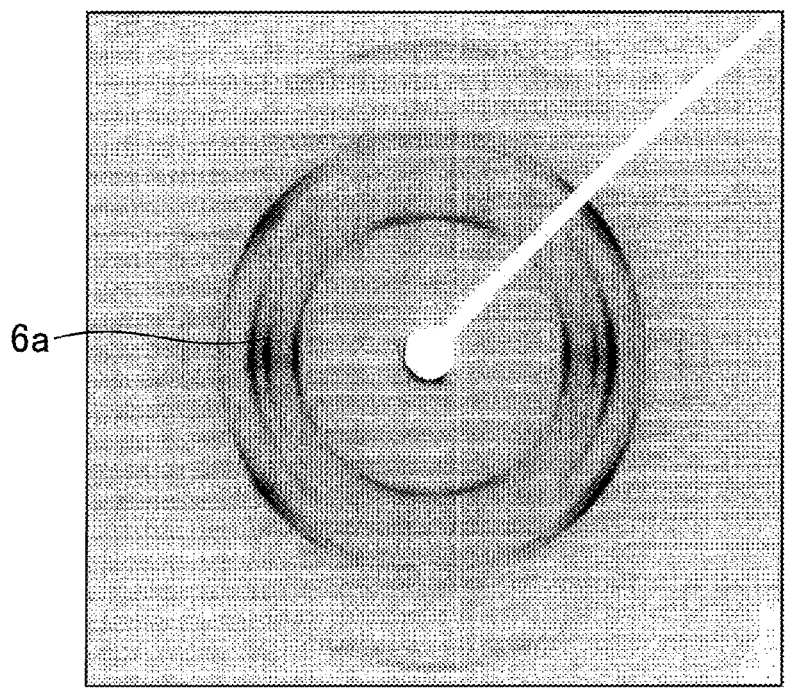
FIG. 15B is a diagram showing an example of the diffraction pattern of a sheet-shaped sample composed of oriented polypropylene.

A sheet-shaped sample composed of unoriented polypropylene and a sheet-shaped sample composed of oriented propylene were measured as measurement examples of samples having different states of orientation, and two X-ray diffraction patterns having different uniformities in the circumferential direction were obtained. FIG. 15A is a view showing an example of the diffraction pattern of a sheet-shaped sample composed of unoriented polypropylene. FIG. 15B is a view showing an example of the diffraction pattern of a sheet-shaped sample composed of oriented polypropylene.

Patterns obtained in the same 2θ position will be compared in relation to the sheet-shaped sample composed of unoriented polypropylene and a sheet-shaped sample composed of oriented propylene. A diffraction pattern 5a of the sheet-shaped sample composed of unoriented polypropylene was a ring shape with uniform intensity in the circumferential direction. In contrast, a diffraction pattern 6a of the sheet-shaped sample composed of oriented polypropylene was a ring shape in which intensity varies periodically in the circumferential direction due to the effect of the oriented aggregate structure. Variation in the intensity of the diffraction pattern 6a was symmetrically depicted.

Figure 16A:
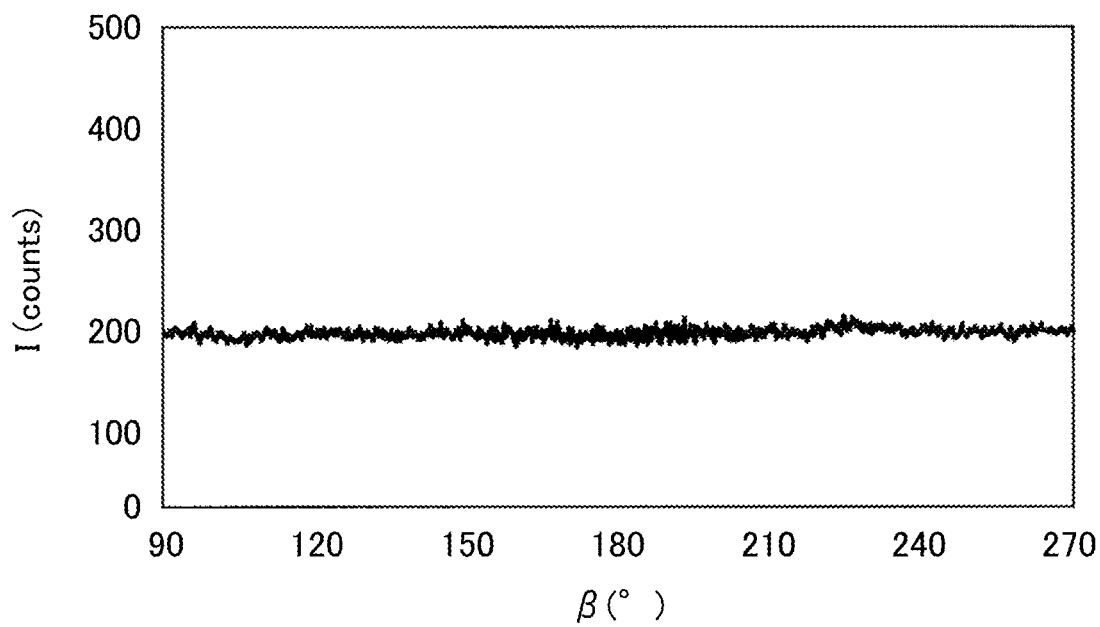
FIG. 16A is a diagram showing the β-I profile of diffraction pattern 5a of FIG. 15A.
Figure 16B:
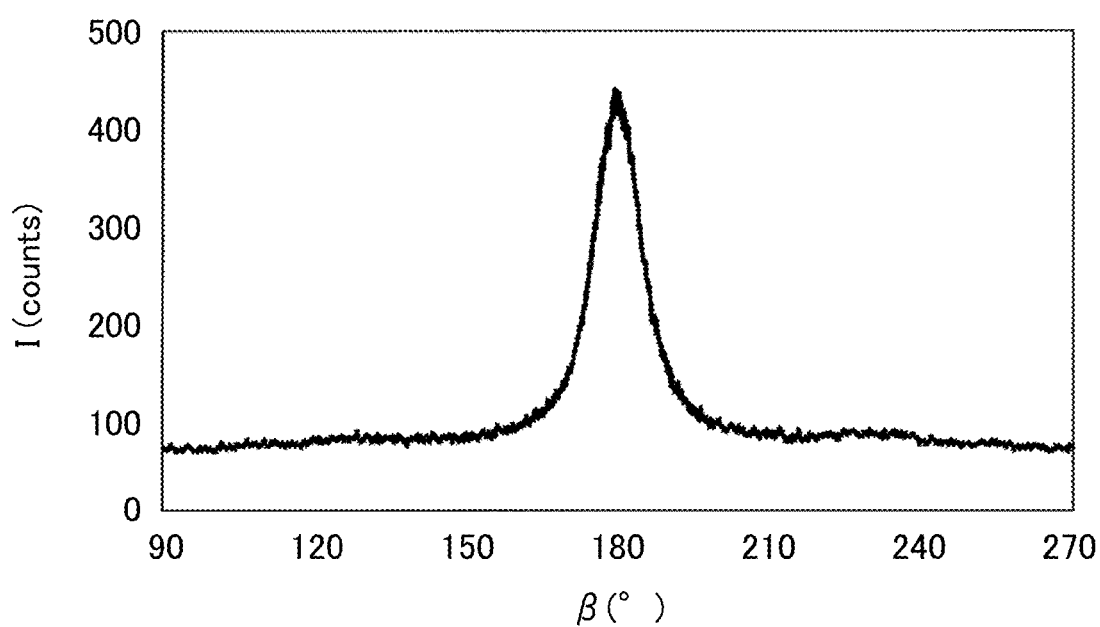
FIG. 16B is a diagram showing the β-I profile of diffraction pattern 6a of FIG. 15B.

FIG. 16A is a diagram showing the β-I profile of diffraction pattern 5a. FIG. 16B is a diagram showing the β-I profile of diffraction pattern 6a. The number of peaks was calculated using the peak-top method for detecting only peaks at 3σ (sigma) or greater from the β-I data of these diffraction patterns, and the number of peaks was found to be "0" in both diffraction patterns. In view of this fact, the ranges of intensity from "0" to the maximum value in the β-I data of the diffraction patterns were divided into 50 to create a histogram.

Figure 17A:
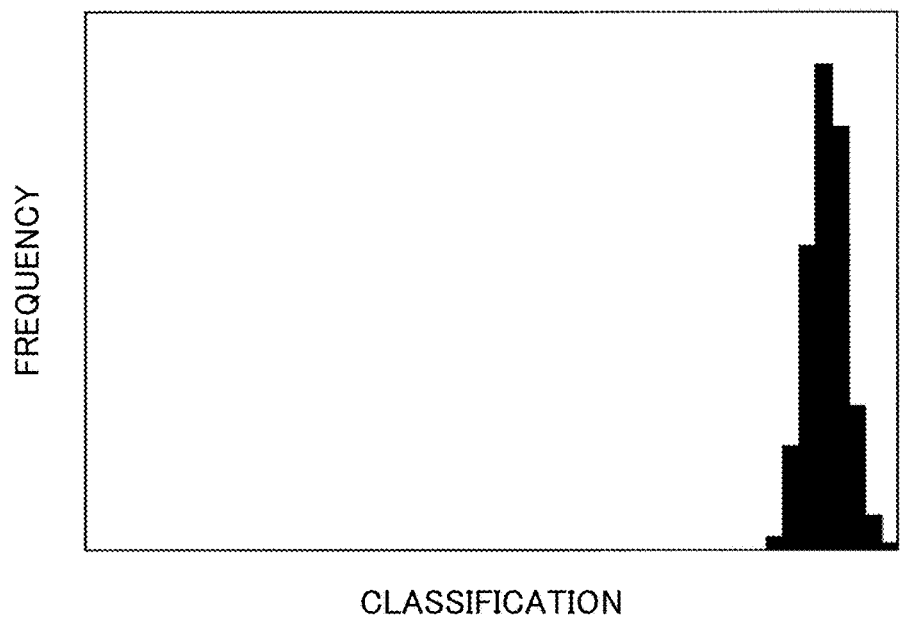
FIG. 17A is a diagram showing a histogram created from the β-I data of the diffraction pattern 5a of FIG. 15A.
Figure 17B:
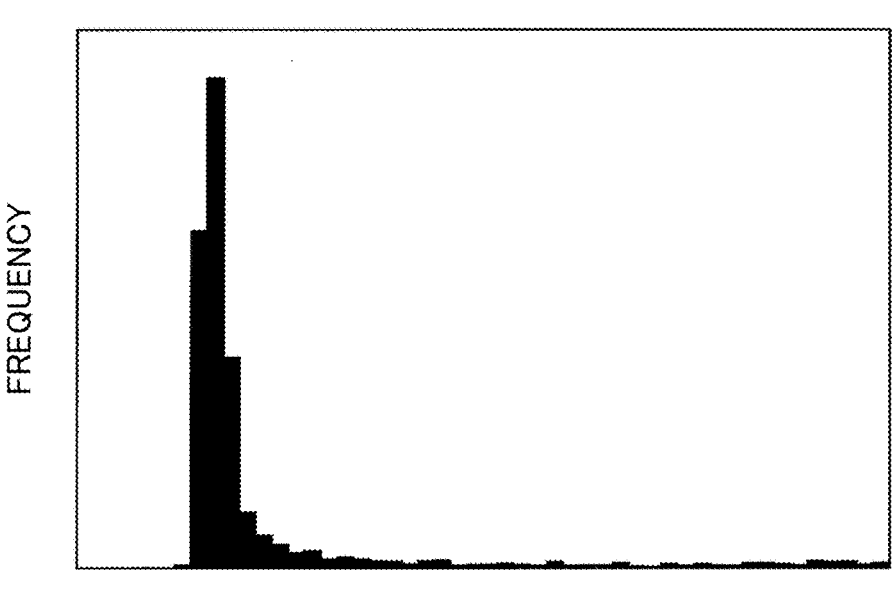
FIG. 17B is a diagram showing a histogram created from the β-I data of the diffraction pattern 6a of FIG. 15B.

FIG. 17A is a diagram showing a histogram created from the β-I of the diffraction pattern 5a. FIG. 17B is a diagram showing a histogram created from the β-I data of the diffraction pattern 6a. FIG. 18 is a diagram showing the following values for the diffraction pattern 5a and diffraction pattern 6a: the characteristics of the values of the number of peaks of the intensity distribution, the characteristics of the values of the skewness Sk of the intensity distribution, the characteristics of the values of the kurtosis Ku of the intensity distribution, the characteristics of the values of the normalized average $X_{norm}$ of the intensity distribution, and the characteristics of the values of the histogram.

The following can be said for the diffraction pattern 5a in which the intensity is uniform in the circumferential direction. Namely, the skewness Sk is a positive value of 4, which suggests a distribution with a long right tail. The kurtosis Ku is a fairly low positive value of 13, which suggests a slightly more peaked distribution than a normal distribution. Also, the normalized average $X_{norm}$ is a very high value 0.91, which suggests a distribution in which the average is biased rightward. In actuality, the shape of the histogram was also rightward and slightly wide.

The following can be said for the diffraction pattern 6a in which the intensity varies periodically in the circumferential direction. Namely, the skewness Sk is a positive value of 4, which suggests a distribution with a long right tail. The kurtosis Ku is a fairly high positive value of 20, which suggests a slightly more peaked distribution than a normal distribution. Also, the normalized average $X_{norm}$ is a low value of 0.23, which suggests a distribution in which the average is biased leftward. In actuality, the shape of the histogram was also leftward and slightly wide.

As described above, the diffraction patterns for which the number of peaks in the β-I profile is calculated to be "0" can be grouped based on the difference in the shapes of the histograms, as well as on the values of the skewness Sk, the kurtosis Ku, and the normalized average $X_{norm}$ in relation to the diffraction patterns in which the number of peaks are calculated to be "0".

(Example of Crystalline Phase Identification Using a Normalized Average and Standard Deviation)

Figure 19:
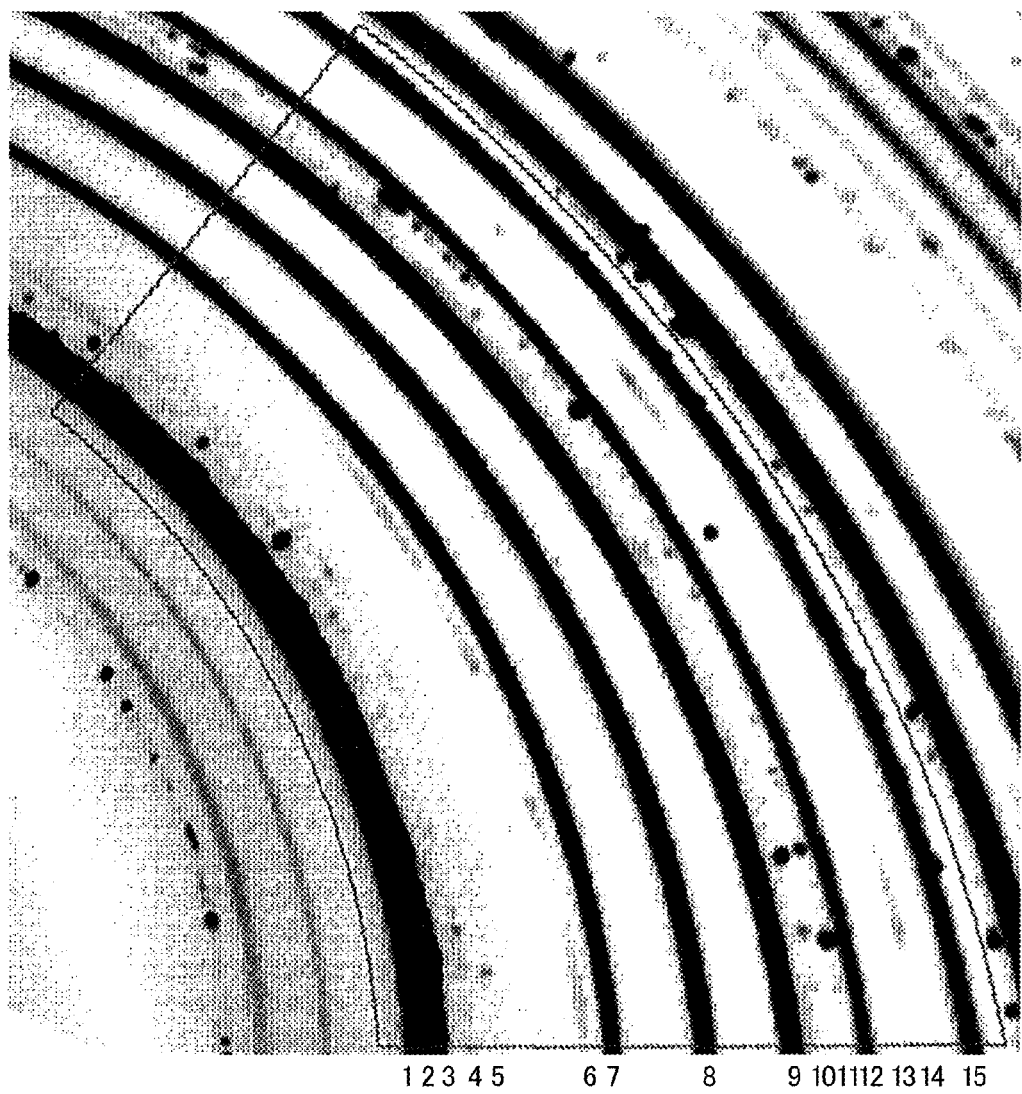
FIG. 19 is a view showing another example of the diffraction pattern of a mixed powder sample of a mineral.
Figure 20:
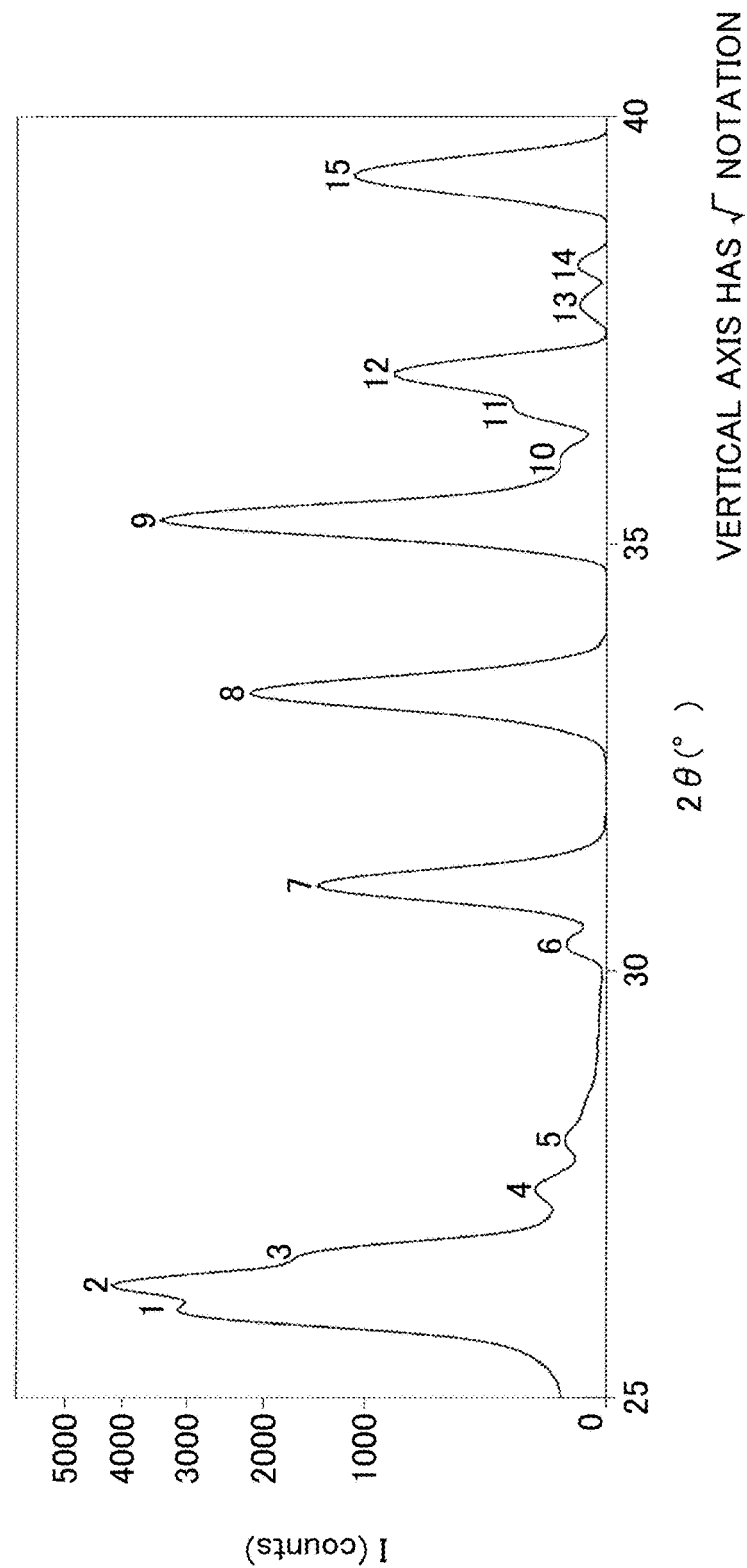
FIG. 20 is a diagram showing the 2θ-I profile of the diffraction pattern shown in FIG. 19.

A mixed powder sample of a mineral was measured while being rotated in an in-plane direction, and X-ray diffraction patterns having a plurality of Debye-Scherrer rings differing in uniformity in the circumferential direction were obtained. FIG. 19 is a view showing another example of the diffraction pattern of a mixed powder sample of a mineral. FIG. 19 contains 15 diffraction patterns numbered 1 to 15 in the range of 2θ=25° to 40°, β=115° to 165° enclosed by a gray outline. FIG. 20 is a diagram showing the 2θ-I profile of the diffraction pattern shown in FIG. 19.

FIG. 21 is a diagram illustrating an example of grouping using the normalized average $X_{norm}$ and standard deviation s as ring characteristic factors. The present example shows an example in which the normalized average $X_{norm}$ and the standard deviation s are calculated as the ring characteristic factors for the diffraction patterns 1 to 15, and grouping the diffraction patterns on the basis thereof.

The diffraction patterns numbered 1, 2, 7, 8, 9, 12, 15 had a normalized average $X_{norm}$ of 0.5 or more and were therefore grouped into the same cluster A. The diffraction patterns numbered 3 and 11 had a normalized average $X_{norm}$ of less than 0.5 and a standard deviation s of 300 or more, and were therefore grouped into the same cluster B. The diffraction patterns numbered 4 and 10 had a normalized average $X_{norm}$ of less than 0.5 and a standard deviation s of 100 or more and less than 300, and were therefore grouped into the same cluster C.

The diffraction pattern numbered 13 had a normalized average $X_{norm}$ of less than 0.5 and a standard deviation s of 50 or more and less than 100, and was therefore grouped into cluster D. The diffraction patterns numbered 5, 6, and 14 had a normalized average $X_{norm}$ of less than 0.5 and a standard deviation s of less than 50, and were therefore grouped into the same cluster E.

As described above, setting a suitable threshold value for each of the ring characteristic factors allows diffraction patterns having different uniformities in the circumferential direction to be grouped into a plurality of clusters.

FIG. 21 is an example showing that the normalized average $X_{norm}$ and the standard deviation s are useful in grouping diffraction patterns, and the grouping conditions of the clusters can be suitably determined in accordance with the numerical values obtained in individual analyses.

Figure 22:
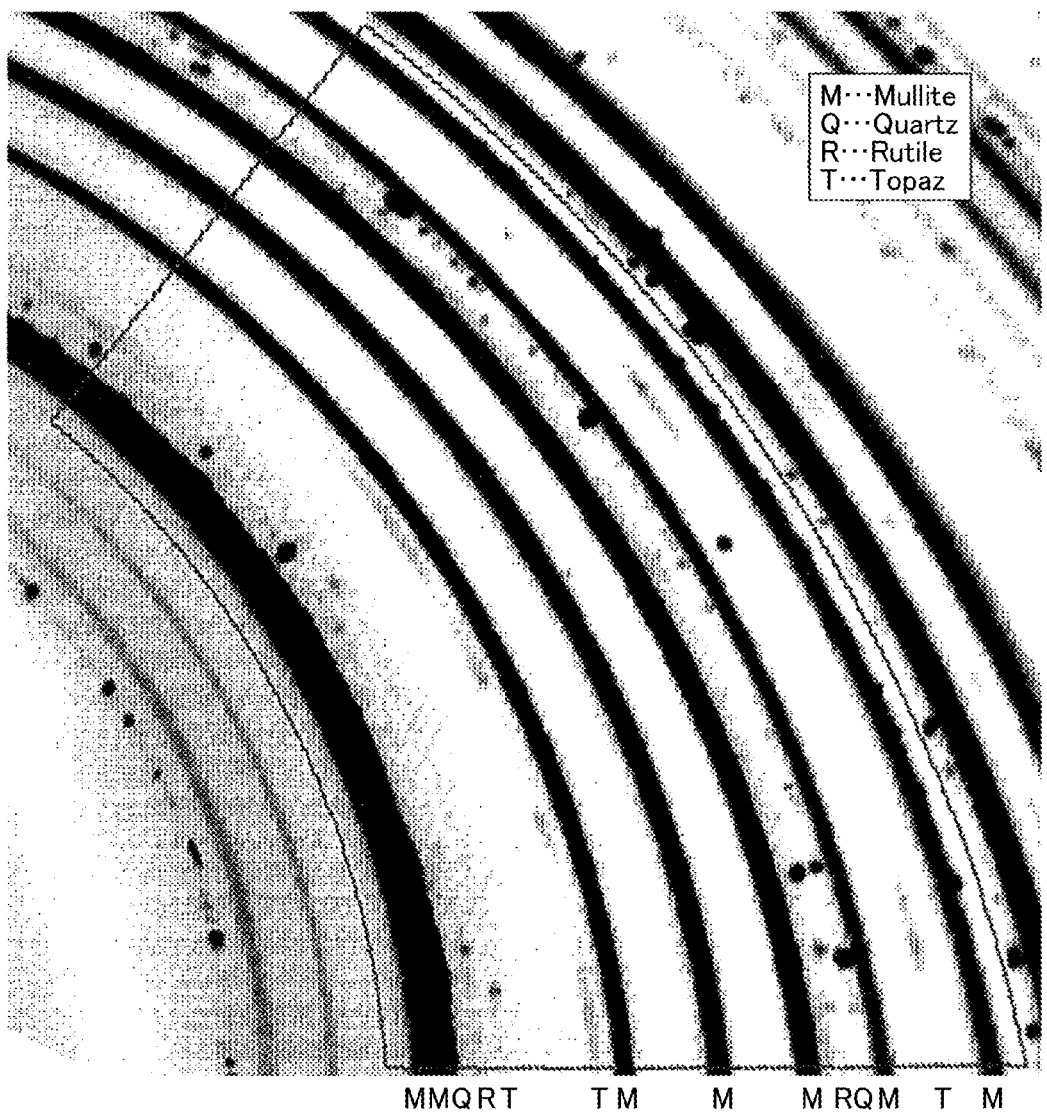
FIG. 22 is a view showing the results of identifying crystalline phases by automatic searching on the basis of the grouping in FIG. 21.

FIG. 22 is a view showing the results of identifying crystalline phases by automatic searching on the basis of the grouping in FIG. 21. Mullite was identified from the sets of peak positions and peak intensity ratios of the diffraction patterns grouped into cluster A. Quartz was identified from the sets of peak positions and peak intensity ratios of the diffraction patterns grouped into cluster B.

Rutile was identified from the sets of peak positions and peak intensity ratios of the diffraction patterns grouped into cluster C. Topaz was identified from the sets of peak positions and peak intensity ratios of the diffraction patterns grouped into cluster E.

(Effects of the First Embodiment)

The following effects can be obtained in accordance with the first embodiment described above.

(1) A search for crystalline phase candidates (step 106 of FIG. 3) is carried out with good precision in the identification of a crystalline phase, and analysis precision can be enhanced.

(2) Furthermore, the ring characteristic factors indicating the homogeneity of the intensity in the diffraction patterns in the circumferential direction are determined from the β-I data of the diffraction patterns. Also, the diffraction patterns are grouped into a plurality of clusters in accordance with the ring characteristic factors thus determined. The grouping thereby clarifies the uniformity of the diffraction patterns in the circumferential direction. Clarifying the uniformity thereby allows diffraction patterns having different uniformities in the circumferential direction to be grouped in to a plurality of clusters.

(3) Moreover, calculating the intensity range R, the standard variance $s^2$, the standard deviation s, or the coefficient of variation CV as ring characteristic factors makes it possible to quantify the degree of uniformity of the diffraction patterns in the circumferential direction.

(4) Furthermore, using the number of peaks and the peak width in the β-I profile as the ring characteristic factors allows diffraction patterns in which the intensity range R, standard variance $s^2$, standard deviation s, or coefficient of variation CV are about the same value to be grouped into different clusters from differences in the number of peaks and the peak width in the β-I profile.

(5) Moreover, using an intensity histogram as the ring characteristic factor allows diffraction patterns in which the intensity range R, standard variance $s^2$, standard deviation s, or coefficient of variation CV are about the same value to be grouped into different clusters on the basis of differences in the histogram. Diffraction patterns in which the number of peaks in the β-I profile is calculated to be "0" can also be grouped on the basis of differences in the histogram.

(6) Furthermore, using the skewness Sk, kurtosis Ku, or normalized average $X_{norm}$ of the intensity distribution as the ring characteristic factors allows characteristics of the intensity distribution to be quantified. The characteristics of the quantified intensity distribution can be used in clustering.

(Second Embodiment)

Figure 23:
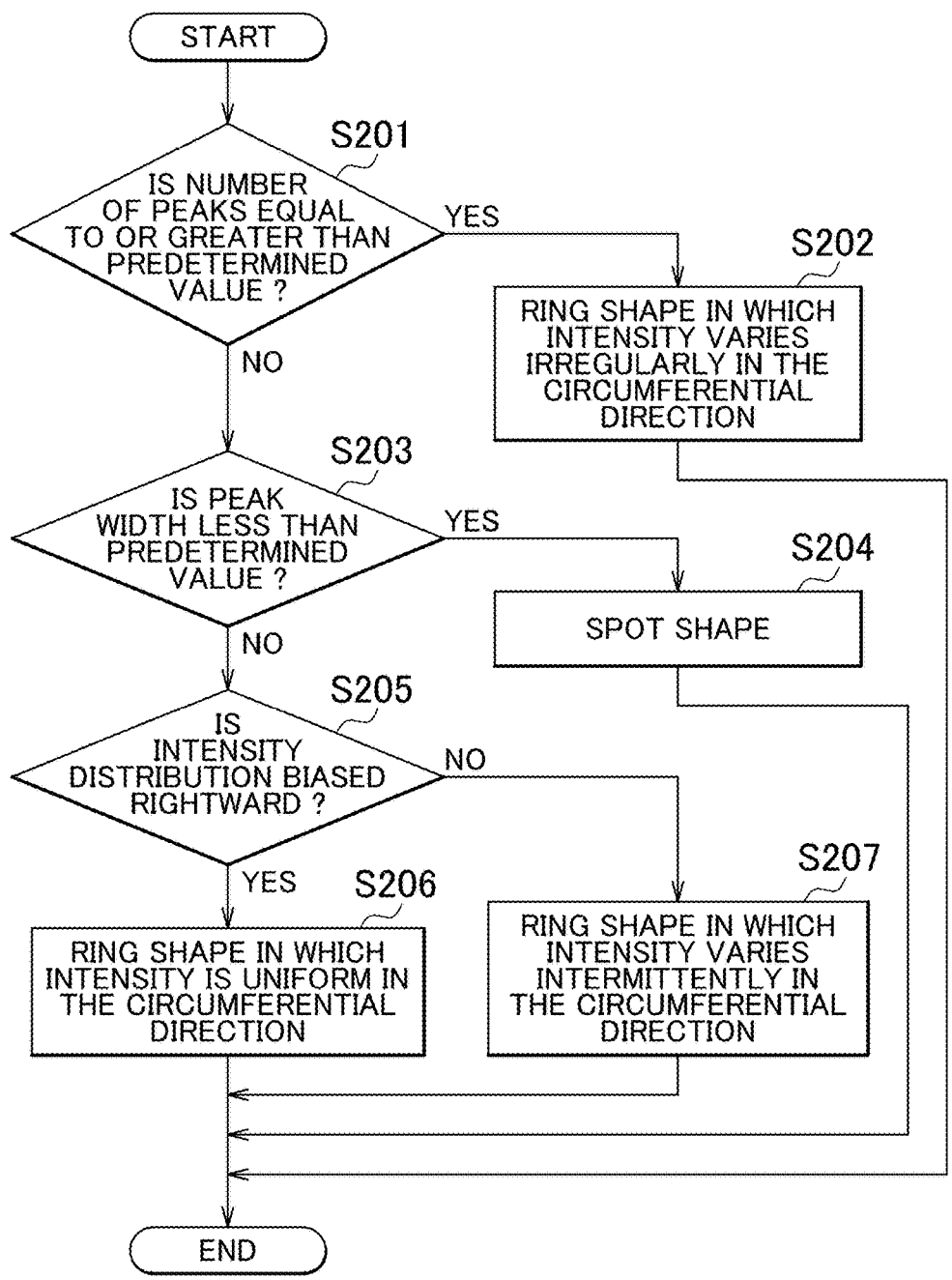
FIG. 23 is a flowchart showing an example of a grouping process using the difference in the number of peaks in a β-I profile, the difference in the peak width in a β-I profile, and the difference in intensity distribution in a second embodiment of the crystalline phase identification method of the present invention.

The configuration of the crystalline phase identification device 20 in a second embodiment of the present invention is similar to or is almost the same as the crystalline phase identification device 20 in the first embodiment described above. FIG. 23 is a flowchart showing an example of a grouping process using the number of peaks in a β-I profile, the peak width in a β-I profile, and the difference in intensity distribution in the second embodiment of the present invention.

The clustering means 26 of the analysis unit 23 first assesses whether the number of peaks in the β-I profile calculated in step 104 of FIG. 3 is equal to or greater than a predetermined value set in advance (step 201). In the case that the number of peaks is equal to or greater than a predetermined value, the clustering means 26 groups the diffraction patterns into a cluster containing ring-shaped diffraction patterns having intensity that varies irregularly in the circumferential direction (step 202).

When the number of peaks is not equal to or greater than a predetermined value ("No" in step 201), the clustering means 26 assesses whether the peak width in the β-I profile calculated in step 104 of FIG. 3 is less than a predetermined set in advance (step 203). When the peak width is less than a predetermined value ("Yes" in step 203), the clustering means 26 groups the diffraction patterns into a cluster containing spot-shaped diffraction patterns (step 204).

When the peak width is not less than a predetermined value ("No" in step 203), the clustering means 26 assesses whether the intensity distribution is biased rightward on the basis of the histogram created in step 104 of FIG. 3 or the calculated normalized average $X_{norm}$ of the intensity distribution (step 205). When the intensity distribution is biased rightward ("Yes" in step 205), the clustering means 26 groups the diffraction patterns into a cluster containing ring-shaped diffraction patterns in which the intensity is uniform in the circumferential direction (step 206).

When the intensity distribution is not biased rightward ("No" in step 205), the clustering means 26 groups the diffraction patterns into a cluster containing ring-shaped diffraction patterns in which the intensity varies intermittently in the circumferential direction (step 207).

(Effects of the Second Embodiment)

In accordance with the second embodiment described above, the diffraction patterns 1a to 4a described as specific examples in the first embodiment can be grouped with good efficiency.

The number of peaks, peak width, and intensity distribution are not always required to be used for grouping in the sequence shown in FIG. 23. The priority order of these ring characteristic factors to be used in grouping can be modified.

(Third Embodiment)

Figure 24:
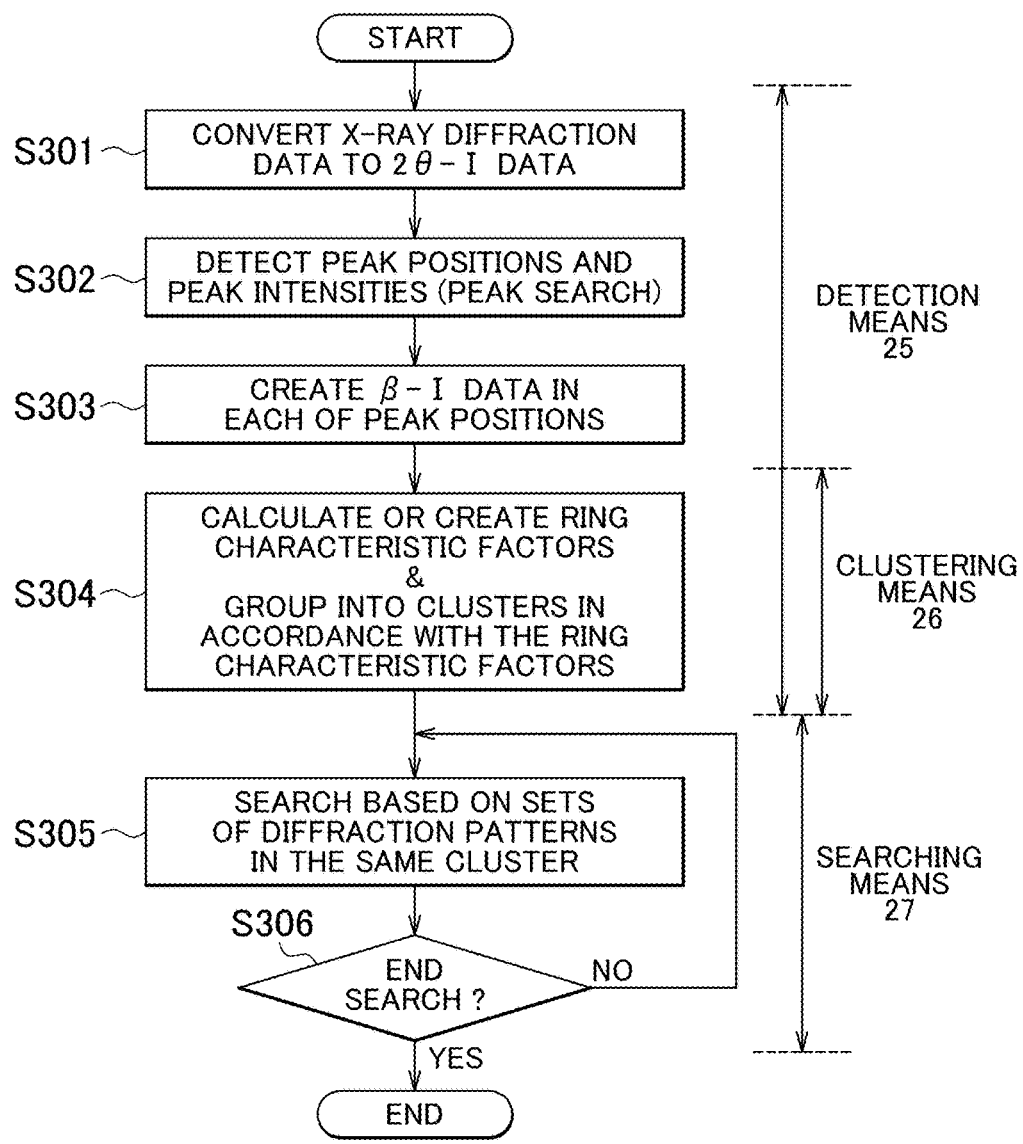
FIG. 24 is a flowchart showing an example of the operation of the analysis unit 23 in a third embodiment of the crystalline phase identification method of the present invention.

The configuration of the crystalline phase identification device 20 in a third embodiment of the present invention is also similar to or is also almost the same as the crystalline phase identification device 20 in the first embodiment described above. FIG. 24 is a flowchart illustrating the operation of the analysis unit 23 in the third embodiment of the present invention. Steps 301 to 303 are the same as steps 101 to 103 of FIG. 3. Step 305 is the same as step 106 of FIG. 3. Step 306 is the same as step 107 of FIG. 3.

In step 304, the detection means 25 of the analysis unit 23 calculates or creates ring characteristic factors on the basis of the β-I data. The clustering means 26 of the analysis unit 23 groups the diffraction patterns into a plurality of clusters in accordance with the ring characteristic factors thus calculated or created.

In the present embodiment, the process of step 104 and the process of step 105 of FIG. 3 in the first embodiment are carried out in combination in the following manner.

Figure 25:
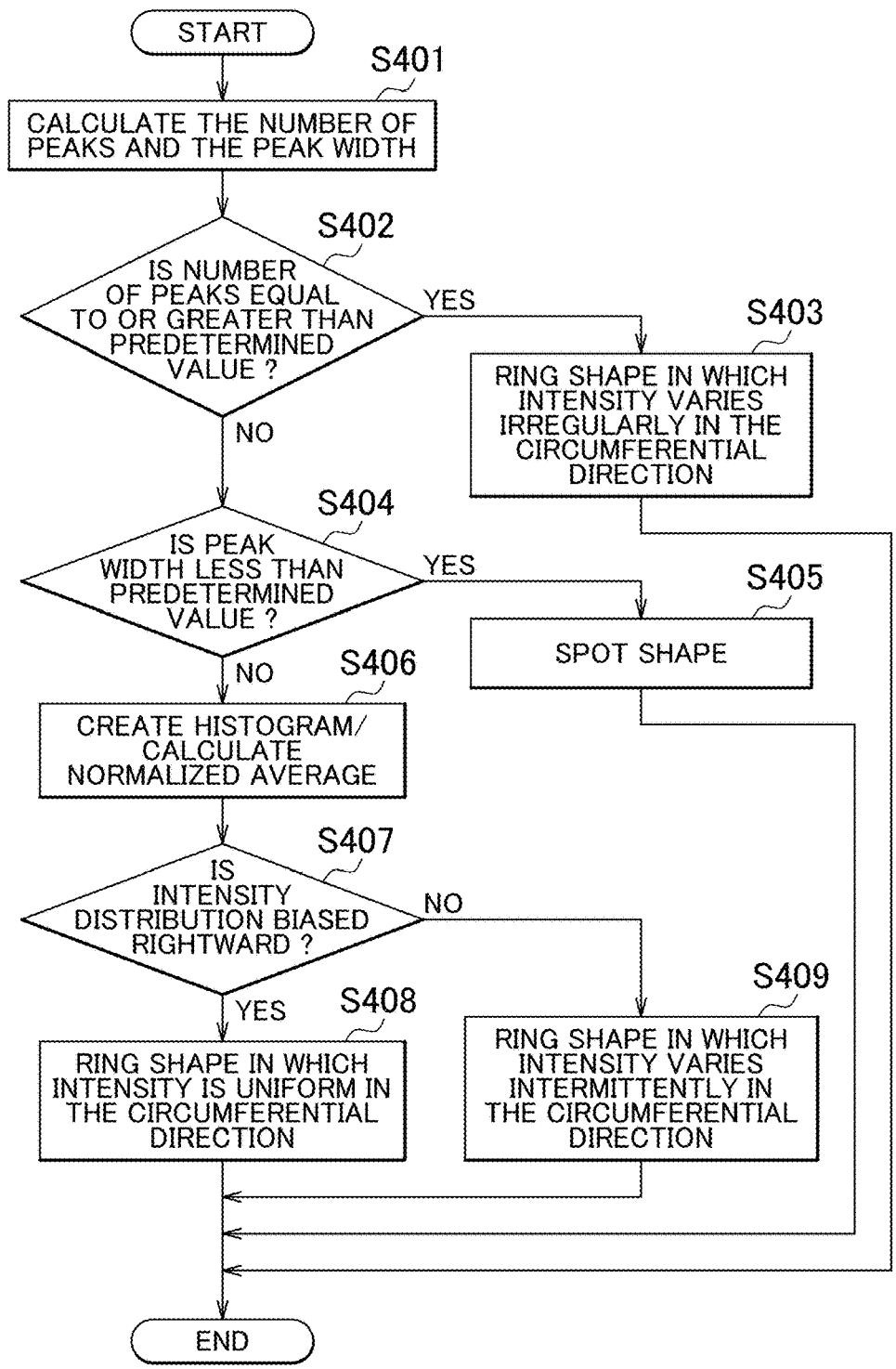
FIG. 25 is a flowchart showing an example of a grouping process using the difference in the number of peaks in a β-I profile, the difference in the peak width in a β-I profile, and the difference in intensity distribution in a third embodiment of the crystalline phase identification method of the present invention.

FIG. 25 is a flowchart illustrating an example of a grouping using differences of the number of peaks in a β-I profile, differences of the peak width in a β-I profile, and differences of the difference in intensity distribution in the third embodiment of the present invention. The detection means 25 calculates the number of peaks and the peak width in the β-I profile from the β-I data (step 401).

The clustering means 26 assesses whether the number of peaks in the β-I profile calculated in step 401 is equal to or greater than a predetermined value set in advance (step 402). When the number of peaks is equal to or greater than the predetermined value ("Yes" in step 402), the clustering means 26 groups the diffraction patterns into a cluster containing ring-shaped diffraction patterns in which the intensity varies irregularly in the circumferential direction (step 403).

When the number of peaks is not equal to or greater than a predetermined value ("No" in step 402), the clustering means 26 assesses whether the peak width in the β-I profile calculated in step 401 is less than a predetermined value set in advance (step 404). When the peak width is less that the predetermined value ("Yes" in step 404), the clustering means 26 groups the diffraction patterns into a cluster containing spot-shaped diffraction patterns (step 405).

When the peak width is not less than the predetermined value ("No" in step 404), the detection means 25 creates an intensity histogram on the basis of the β-I data, or calculates the normalized average $X_{norm}$ of the intensity distribution (step 406). The clustering means 26 assesses whether the intensity distribution is biased rightward on the basis of the histogram created in step 406 or the calculated normalized average $X_{norm}$ of the intensity distribution (step 407).

When the intensity distribution is biased rightward ("Yes" in step 407) the clustering means 26 groups the diffraction patterns into a cluster containing ring-shaped diffraction patterns in which the intensity is uniformed in the circumferential direction (step 408). When the intensity distribution is not biased rightward ("No" in step 407), the clustering means 26 groups the diffraction patterns into a cluster containing ring-shaped diffraction patterns in which the intensity varies intermittently in the circumferential direction (step 409).

(Effects of the Third Embodiment)

In accordance with the third embodiment, the effects of the second embodiment described above can be obtained. Furthermore, in accordance with the third embodiment, a histogram or the normalized average $X_{norm}$ of the intensity distribution is not used as a ring characteristic factor. Moreover, in accordance with the third embodiment, creation or calculation of diffraction patterns that can be grouped is not required. Thus, in the third embodiment, diffraction pattern grouping can be carried out more rapidly because a histogram or the normalized average $X_{norm}$ of the intensity distribution is not used as a ring characteristic factor and there is no need to create or calculate diffraction patterns that can be grouped.

(Other Embodiments)

In the present invention, other elements that express homogeneity of intensity of Debye-Scherrer rings in the circumferential direction may be used as ring characteristic factors in addition to those described above.

DESCRIPTION OF SYMBOLS 1a, 2a, 3a, 4a, 5a, 6a: diffraction patterns; 10: X-ray diffractometer; 11: sample; 12: goniometer; 13: X-ray generator; 14: collimator; 15: X-ray detector; 16: control unit; 17: input/output device; 20: crystalline phase identification device; 21: input means; 22: storage unit; 23: analysis unit; 24: output means; 25: detection means; 26; clustering means; 27: searching means; 30: display device

The invention claimed is:

1. A crystal phase identification method for identifying a crystal phase contained in a sample, the method comprising:
   generating x-rays, by an x-ray generator of an x-ray diffractometer within an x-ray diffraction measurement system, and irradiating the generating x-rays on the sample;
   detecting, by an x-ray detector of the x-ray diffractometer, x-rays diffracted by the sample;
   transmitting, via an output device, of the x-ray diffractometer, X-ray diffraction data to a crystalline phase identification device of the x-ray diffraction measurement system, wherein said x-ray diffraction data contains data of a plurality of ring-shaped diffraction patterns,
   detecting, by a central processing unit of the crystalline phase identification device, peak positions in a 2θ direction and peak intensities in the 2θ direction for the plurality of ring-shaped diffraction patterns from the X-ray diffraction data;
   based on circumferential angles of the ring-shaped diffraction patterns of the plurality of ring-shaped diffraction patterns, creating, by the central processing unit, circumferential angle versus intensity data for the plurality of ring-shaped diffraction patterns in the peak positions of a 2θ-I profile;
   grouping, by the central processing unit of the crystalline phase identification device, the ring-shaped diffraction patterns of the plurality of ring-shaped diffraction patterns into a plurality of clusters on a basis of the created circumferential angle versus intensity data;
   extracting, by the central processing unit, from a database of the crystalline phase identification device, crystalline phases that demonstrate peak positions and peak intensity ratios corresponding to the peak positions and peak intensity ratios of the ring-shaped diffraction patterns grouped into the same cluster, and
   displaying, by the central processing unit, on a display device, the extracted crystalline phases.

2. The crystal phase identification method according to claim 1, further comprising:
   determining ring characteristic factors representing homogeneity of intensity in the circumferential direction of the diffraction patterns from the circumferential angle versus intensity data of the plurality of ring-shaped diffraction patterns, and grouping the diffraction patterns of the plurality of ring-shaped diffraction patterns into a plurality of clusters in accordance with the ring characteristic factors thus determined.

3. The crystal phase identification method according to claim 2,
wherein an intensity range, a standard variance, a standard deviation, or a coefficient of variation, where intensity is a variate, are calculated as the ring characteristic factors from the circumferential angle versus intensity data of the plurality of ring-shaped diffraction patterns.

4. The crystal phase identification method according to claim 2, wherein a number of peaks and a peak width in a circumferential angle versus intensity profile are calculated as the ring characteristic factors from the circumferential angle versus intensity data of the plurality of ring-shaped diffraction patterns.

5. The crystal phase identification method according to claim 2,
wherein an intensity histogram is created as the ring characteristic factor from the circumferential angle versus intensity data of the plurality of ring-shaped diffraction patterns.

6. The crystal phase identification method according to claim 2,
wherein a skewness, kurtosis, or normalized average of the intensity distribution are calculated as the ring characteristic factors from the circumferential angle versus intensity data of the plurality of ring-shaped diffraction patterns.

7. An x-ray diffraction measurement system for identifying a crystal phase contained in a sample, comprising:
an x-ray diffractometer including an x-ray generator, an x-ray detector, and an output device, wherein
the x-ray diffractometer is configured to generate x-rays, via the x-ray generator, and irradiate the generated x-rays on the sample,
the x-ray detector detects x-rays diffracted by the sample, and
the output device outputs x-ray diffraction data, wherein the x-ray diffraction data contains data of a plurality of ring-shaped diffraction patterns, and
a crystalline phase identification device including a central processing unit and a database device, wherein the central processing unit is configured to
detect peak positions in a 2θ-direction and peak intensities in the 2θ-direction for the plurality of ring-shaped diffraction patterns from the X-ray diffraction data,
create, based on circumferential angles of the ring-shaped diffraction patterns of the plurality of ring-shaped diffraction patterns, circumferential angle versus intensity data for the plurality of the plurality of ring-shaped diffraction patterns in the peak positions of a 2θ-I profile, group the diffraction patterns of the plurality of ring-shaped diffraction patterns into a plurality of clusters on a basis of the created circumferential angle versus intensity data,
extract, from the database device, stored crystalline phases that demonstrate peak positions and peak intensity ratios corresponding to the peak positions and peak intensity ratios of the plurality of ring-shaped diffraction patterns grouped into the same cluster, and
display, on a display device, the extracted crystalline phases.

8. The crystal phase identification device according to claim 7, wherein:
the detection means determines ring characteristic factors representing homogeneity of intensity in the circumferential direction of the plurality of ring-shaped diffraction patterns, from the circumferential angle versus intensity data of the plurality of ring-shaped diffraction patterns, and
the clustering means groups the ring-shaped diffraction patterns of the plurality of plurality of ring-shaped into a plurality of clusters in accordance with the ring characteristic factors determined by the detection means.

9. The crystal phase identification device according to claim 8,
wherein the detection means calculates an intensity range, a standard variance, a standard deviation, or a coefficient of variation, where intensity is a variate, are calculated as the ring characteristic factors from the circumferential angle versus intensity data of the plurality of ring-shaped diffraction patterns.

10. The crystal phase identification device according to claim 8,
wherein the detection means calculates a number of peaks and a peak width in a circumferential angle versus intensity profile as the ring characteristic factors from the circumferential angle versus intensity data of the plurality of ring-shaped diffraction patterns.

11. The crystal phase identification device according to claim 8, wherein the detection means creates an intensity histogram as the ring characteristic factor from the circumferential angle versus intensity data of the plurality of ring-shaped diffraction patterns.

12. The crystal phase identification device according to claim 8, wherein the detection means calculates a skewness, kurtosis, or normalized average of the intensity distribution as the ring characteristic factors from the circumferential angle versus intensity data of the plurality of ring-shaped diffraction patterns.

* * * * *